(12) United States Patent
Maxwell et al.

(10) Patent No.: US 8,758,994 B2
(45) Date of Patent: Jun. 24, 2014

(54) CDK9 AS MODIFIER OF THE IGF PATHWAY AND METHODS OF USE

(75) Inventors: Mark E. Maxwell, Lansdale, PA (US); Michael Martin Ollmann, Redwood City, CA (US); Timothy S. Heuer, El Granada, CA (US); Lynn Margaret Bjerke, Sutton (GB)

(73) Assignee: Exelixis, Inc., South San Francisco, CA (US)

( * ) Notice: Subject to any disclaimer, the term of this patent is extended or adjusted under 35 U.S.C. 154(b) by 1607 days.

(21) Appl. No.: 11/628,636

(22) PCT Filed: Jun. 20, 2005

(86) PCT No.: PCT/US2005/021630
§ 371 (c)(1),
(2), (4) Date: Dec. 13, 2007

(87) PCT Pub. No.: WO2006/009933
PCT Pub. Date: Jan. 26, 2006

(65) Prior Publication Data
US 2008/0095763 A1    Apr. 24, 2008

Related U.S. Application Data

(60) Provisional application No. 60/581,689, filed on Jun. 21, 2004.

(51) Int. Cl.
*C12Q 1/68* (2006.01)
*G01N 33/53* (2006.01)

(52) U.S. Cl.
USPC .............................. 435/6.1; 435/6.17; 435/7.1

(58) Field of Classification Search
None
See application file for complete search history.

(56) References Cited

U.S. PATENT DOCUMENTS

2004/0082613 A1    4/2004 Schneider et al.
2004/0110140 A1*   6/2004 Bennett et al. ............... 435/6

FOREIGN PATENT DOCUMENTS

| WO | WO 96/28555 A | 9/1996 |
| WO | WO 03/003906 A | 1/2003 |
| WO | WO 03/100008 A | 12/2003 |

OTHER PUBLICATIONS

Kappel et al. Current Opinion in Biotechnology 3:548-553, 1992.*
Cameron Molecular Biotechnology 7:253-265, 1997.*
Houdebine Journal of Biotechnology 98:145-160, 2002.*
Patrick H. Maxwell et al.: "Activation of The IF Pathway in Cancer," Current Opinion in Genetics and Development, vol. 11, No. 3, Jun. 2001, pp. 293-299.
Yu, He, et al., "Plasma Levels of Insulin-like Growth Factor-1 and Lung Cancer Risk: a Case-control Analysis.", Journal of the National Cancer Institute, Jan. 20, 1999, vol. 91, No. 2, pp. 151-156.
Stambolic, et al., "Negative Regulation of PKB/Akt-Dependent Cell Survival by the Tumor Suppressor PTEN.", Cell, Oct. 2, 1998, vol. 95, pp. 29-39.
Genbank Identifier No. 17017983, entitled: "*Homo sapiens* RAR-related orphan receptor A (RORA), transcript variant 3, mRNA," dated Dec. 20, 2003, 4 pages.
Genbank Identifier No. 12805028, entitled: "*Homo sapiens* cyclin-dependent kinase 9, mRNA (cDNA clone MGC:5166 Image:3460767), complete cds," dated Feb. 3, 2004, 3 pages.
Genbank Identifier No. 8099629, entitled: "*Homo sapiens* protein kinase CDK9 (CDK9) gene, complete cds," dated Jul. 31, 2000, 2 pages.
Genbank Identifier No. 599828, entitled: "*H. sapiens* mRNA (clone C-2k) mRNA for serine/threonine protein kinase," dated Jul. 21, 1995, 2 pages.
Genbank Identifier No. 54696667, entitled: "*Homo sapiens* cyclin-dependent kinase 9 (CDC2-related kinase) mRNA, complete cds," dated Oct. 28, 2004, 2 pages.
Genbank Identifier No. 4502747, entitled: "cyclin-dependent kinase 9 [*Homo sapiens*]," dated Dec. 21, 2003, 4 pages.

* cited by examiner

*Primary Examiner* — Tekchand Saidha
*Assistant Examiner* — Md. Younus Meah
(74) *Attorney, Agent, or Firm* — McDonnell Boehnen Hulbert & Berghoff LLP

(57) ABSTRACT

Human CDK9 genes are identified as modulators of the IGF pathway, and thus are therapeutic targets for disorders associated with defective IGF function. Methods for identifying modulators of IGF, comprising screening for agents that modulate the activity of CDK9 are provided.

6 Claims, No Drawings

CDK9 AS MODIFIER OF THE IGF PATHWAY AND METHODS OF USE

REFERENCE TO RELATED APPLICATIONS

This application claims priority to U.S. provisional patent application 60/581,689 filed Jun. 21, 2004. The contents of the prior application are hereby incorporated in their entirety.

BACKGROUND OF THE INVENTION

Somatic mutations in the PTEN (Phosphatase and Tensin homolog deleted on chromosome 10) gene are known to cause tumors in a variety of human tissues. In addition, germline mutations in PTEN are the cause of human diseases (Cowden disease and Bannayan-Zonana syndrome) associated with increased risk of breast and thyroid cancer (Nelen M R et al. (1997) Hum Mol Genet, 8:1383-1387; Liaw D et al. (1997) Nat Genet, 1:64-67; Marsh D J et al. (1998) Hum Mol Genet, 3:507-515). PTEN is thought to act as a tumor suppressor by regulating several signaling pathways through the second messenger phosphatidylinositol 3,4,5 triphosphate (PIP3). PTEN dephosphorylates the D3 position of PIP3 and downregulates signaling events dependent on PIP3 levels (Maehama T and Dixon J E (1998) J Biol Chem, 22, 13375-8). In particular, pro-survival pathways downstream of the insulin-like growth factor (IGF) pathway are regulated by PTEN activity. Stimulation of the IGF pathway, or loss of PTEN function, elevates PIP3 levels and activates pro-survival pathways associated with tumorigenesis (Stambolic V et al. (1998) Cell, 95:29-39). Consistent with this model, elevated levels of insulin-like growth factors I and II correlate with increased risk of cancer (Yu H et al (1999) J Natl Cancer Inst 91:151-156) and poor prognosis (Takanami I et al, 1996, J Surg Oncol 61(3):205-8).

PTEN sequence is conserved in evolution, and exists in mouse (Hansen GM and Justice M J (1998) Mamm Genome, 9(1):88-90), *Drosophila* (Goberdhan D C et al (1999) Genes and Dev, 24:3244-58; Huang H et al (1999) Development 23:5365-72), and *C. elegans* (Ogg S and Ruvkun G, (1998) Mol Cell, (6):887-93). Studies in these model organisms have helped to elucidate the role of PTEN in processes relevant to tumorigenesis. In *Drosophila*, the PTEN homolog (dPTEN) has been shown to regulate cell size, survival, and proliferation (Huang et al, supra; Goberdhan et al, supra; Gao X et al, 2000, 221:404-418). In mice, loss of PTEN function increases cancer susceptibility (Di Cristofano A et al (1998) Nature Genetics, 19:348-355; Suzuki A et al (1998) Curr. Biol., 8:1169-78).

In addition, a member of the IGF/insulin receptor family exists in *Drosophila* and has been shown to respond to insulin stimulation (Femandez-Almonacid R, and Rozen O M (1987) Mol Cell Bio, (8):2718-27). Similar to PTEN, studies in *Drosophila* (Brogiolo W et al (2001) Curr Biol, 11(4):213-21) and mouse (Moorehead R A et al (2003) Oncogene, 22(6):853-857) establish a conserved role for the IGF/insulin pathway in growth control.

cyclin-dependent kinase 9 (CDK9) is a member of the cyclin-dependent protein kinase (CDK) family. CDK family members are highly similar to the gene products of *S. cerevisiae* cdc28, and *S. pombe* cdc2, and known as important cell cycle regulators. CDK9 was found to be a component of the multiprotein complex TAK/P-TEFb, which is an elongation factor for RNA polymerase II-directed transcription and functions by phosphorylating the C-terminal domain of the largest subunit of RNA polymerase II. CDK9 forms a complex with and is regulated by its regulatory subunit cyclin T or cyclin K. HIV-1 Tat protein was found to interact with this protein and cyclin T, which suggested a possible involvement of this protein in AIDS.

The ability to manipulate the genomes of model organisms such as *Drosophila* provides a powerful means to analyze biochemical processes that, due to significant evolutionary conservation, have direct relevance to more complex vertebrate organisms. Due to a high level of gene and pathway conservation, the strong similarity of cellular processes, and the functional conservation of genes between these model organisms and mammals, identification of the involvement of novel genes in particular pathways and their functions in such model organisms can directly contribute to the understanding of the correlative pathways and methods of modulating them in mammals (see, for example, Mechler B M et al., 1985 EMBO J 4:1551-1557; Gateff E. 1982 Adv. Cancer Res. 37: 33-74; Watson K L., et al., 1994 J Cell Sci. 18: 19-33; Miklos G L, and Rubin G M. 1996 Cell 86:521-529; Wassarman D A, et al., 1995 Curr Opin Gen Dev 5: 44-50; and Booth D R. 1999 Cancer Metastasis Rev. 18: 261-284). For example, a genetic screen can be carried out in an invertebrate model organism or cell having underexpression (e.g. knockout) or overexpression of a gene (referred to as a "genetic entry point") that yields a visible phenotype, such as altered cell growth. Additional genes are mutated in a random or targeted manner. When a gene mutation changes the original phenotype caused by the mutation in the genetic entry point, the gene is identified as a "modifier" involved in the same or overlapping pathway as the genetic entry point. When inactivation of either gene is not lethal, but inactivation of both genes results in reduced viability or death of the cell, tissue, or organism, the interaction is defined as "synthetic lethal" (Bender, A and Pringle J, (1991) Mol Cell Biol, 11:1295-1305; Hartman J et al, (2001) Science 291:1001-1004; U.S. Pat. No. 6,489,127). In a synthetic lethal interaction, the modifier may also be identified as an "interactor". When the genetic entry point is an ortholog of a human gene implicated in a disease pathway, such as the IGF pathway, modifier genes can be identified that may be attractive candidate targets for novel therapeutics.

All references cited herein, including patents, patent applications, publications, and sequence information in referenced Genbank identifier numbers, are incorporated herein in their entireties.

SUMMARY OF THE INVENTION

We have discovered genes that modify the IGF pathway in *Drosophila* cells, and identified their human orthologs, hereinafter referred to as cyclin dependent kinase 9 (CDK9). The invention provides methods for utilizing these IGF modifier genes and polypeptides to identify CDK9-modulating agents that are candidate therapeutic agents that can be used in the treatment of disorders associated with defective or impaired IGF function and/or CDK9 function. Preferred CDK9-modulating agents specifically bind to CDK9 polypeptides and restore IGF function. Other preferred CDK9-modulating agents are nucleic acid modulators such as antisense oligomers and RNAi that repress CDK9 gene expression or product activity by, for example, binding to and inhibiting the respective nucleic acid (i.e. DNA or mRNA).

CDK9 modulating agents may be evaluated by any convenient in vitro or in vivo assay for molecular interaction with a CDK9 polypeptide or nucleic acid. In one embodiment, candidate CDK9 modulating agents are tested with an assay system comprising a CDK9 polypeptide or nucleic acid. Agents that produce a change in the activity of the assay system relative to controls are identified as candidate IGF modulating agents. The assay system may be cell-based or cell-free. CDK9-modulating agents include CDK9 related proteins (e.g. dominant negative mutants, and biotherapeutics); CDK9-specific antibodies; CDK9-specific antisense oligomers and other nucleic acid modulators; and chemical agents that specifically bind to or interact with CDK9 or compete with CDK9 binding partner (e.g. by binding to a CDK9 binding partner). In one specific embodiment, a small molecule modulator is identified using a kinase assay. In specific embodiments, the screening assay system is selected from a binding assay, an apoptosis assay, a cell proliferation assay, an angiogenesis assay, and a hypoxic induction assay.

In another embodiment, candidate IGF pathway modulating agents are further tested using a second assay system that detects changes in the IGF pathway, such as angiogenic, apoptotic, or cell proliferation changes produced by the originally identified candidate agent or an agent derived from the original agent. The second assay system may use cultured cells or non-human animals. In specific embodiments, the secondary assay system uses non-human animals, including animals predetermined to have a disease or disorder implicating the IGF pathway, such as an angiogenic, apoptotic, or cell proliferation disorder (e.g. cancer).

The invention further provides methods for modulating the CDK9 function and/or the IGF pathway in a mammalian cell by contacting the mammalian cell with an agent that specifically binds a CDK9 polypeptide or nucleic acid. The agent may be a small molecule modulator, a nucleic acid modulator, or an antibody and may be administered to a mammalian animal predetermined to have a pathology associated with the IGF pathway.

DETAILED DESCRIPTION OF THE INVENTION

The PTEN co-RNAi plus insulin synthetic interaction screen was designed to identify modifier genes that are lethal or reduce proliferation in cells with a hyperstimulated IGF/insulin pathway, but not in normal cells. We refer to these genes as "synthetic lethal" genes in the context of this screen. To identify these genes, we created cells with a hyperstimulated IGF/insulin pathway by treatment with insulin and RNAi-mediated inactivation of dPTEN, the *Drosophila* homologue of the human tumor suppressor PTEN. In addition to identifying genes with synthetic lethal interactions in insulin-treated, PTEN-deficient cells, this screen identified genes that, when inactivated, preferentially suppressed multiple readouts known to be regulated by IGF signaling. For our screen, these readouts included an expression assay for a IGF/insulin reporter gene and quantitative Western blot readouts for several nodes in the IGF/insulin pathway (phospho-4E-BP, phospho-MAPK, phospho-S6K, and total RpS6).

In a preferred embodiment, the *Drosophila* IGF modifier screen identified genes that, when inactivated, preferentially suppressed insulin-induced Lactate Dehydrogenase (LDH) expression and hence may be key mediators of IGF/PTEN signaling. Lactate Dehydrogenase (LDH) is a well-validated target of the *Drosophila* Insulin/IGF pathway. We confirmed this finding by analyzing gene expression in insulin-stimulated *Drosophila* S2 cells by microarray expression analysis (Affymetrix), which showed significant increases in expression of the LDH gene. This result was confirmed by Quantitative PCR (Taqman®) assay that detected a 12-fold increase in LDH expression in cells treated with either 1 μM insulin or dsRNA specific to the dPTEN gene. The use of LDH as a reporter gene has also been validated by RNAi of known positive mediators of IGF signaling such as InR, IRS, Tor, and Rheb, which results in substantially decreased LDH expression in the assay. In contrast, RNAi of known negative regulators of IGF signaling (TSC1 and TSC2) results in an increase in LDH expression; To further confirm that modifiers that decrease insulin-induced expression of LDH have relevance to IGF/PTEN signaling, we performed Quantitative Western Blots to determine whether RNAi of each modifier decreased phosphorylation of 4E-BP (a downstream gene that is phosphorylated by the Tor kinase) or affected S6K (Thr389) phosphorylation, MAPK phosphorylation, or total RPS6 protein levels. The CG5179-PA gene was identified as a modifier of the IGF pathway. Accordingly, vertebrate orthologs of this modifier, and preferably the human orthologs, CDK9 genes (i.e., nucleic acids and polypeptides) are attractive drug targets for the treatment of pathologies associated with a defective IGF signaling pathway, such as cancer.

In vitro and in vivo methods of assessing CDK9 function are provided herein. Modulation of the CDK9 or their respective binding partners is useful for understanding the association of the IGF pathway and its members in normal and disease conditions and for developing diagnostics and therapeutic modalities for IGF related pathologies. CDK9-modulating agents that act by inhibiting or enhancing CDK9 expression, directly or indirectly, for example, by affecting a CDK9 function such as enzymatic (e.g., catalytic) or binding activity, can be identified using methods provided herein. CDK9 modulating agents are useful in diagnosis, therapy and pharmaceutical development.

Nucleic Acids and Polypeptides of the Invention

Sequences related to CDK9 nucleic acids and polypeptides that can be used in the invention are disclosed in Genbank (referenced by Genbank identifier (GI) number) as GI#s 17017983 (SEQ ID NO:1), 12805028 (SEQ ID NO:2), 8099629 (SEQ ID NO:3), 599828 (SEQ ID NO:4), and 54696667 (SEQ ID NO:5) for nucleic acid, and GI#4502747 (SEQ ID NO:6) for polypeptide sequences.

The term "CDK9 polypeptide" refers to a full-length CDK9 protein or a functionally active fragment or derivative thereof. A "functionally active" CDK9 fragment or derivative exhibits one or more functional activities associated with a full-length, wild-type CDK9 protein, such as antigenic or immunogenic activity, enzymatic activity, ability to bind natural cellular substrates, etc. The functional activity of CDK9 proteins, derivatives and fragments can be assayed by various methods known to one skilled in the art (Current Protocols in Protein Science (1998) Coligan et al., eds., John Wiley & Sons, Inc., Somerset, N.J.) and as further discussed below. In one embodiment, a functionally active CDK9 polypeptide is a CDK9 derivative capable of rescuing defective endogenous CDK9 activity, such as in cell based or animal assays; the rescuing derivative may be from the same or a different species. For purposes herein, functionally active fragments also include those fragments that comprise one or more structural domains of a CDK9, such as a kinase domain or a binding domain. Protein domains can be identified using the PFAM program (Bateman A., et al., Nucleic Acids Res, 1999, 27:260-2). For example, the kinase domain (PFAM00069) of CDK9 from GI#4502747 (SEQ ID NO:6) is located at approximately amino acid residues 19 to 315. Methods for obtaining CDK9 polypeptides are also further described below. In some embodiments, preferred fragments are functionally active, domain-containing fragments comprising at least 25 contiguous amino acids, preferably at least 50, more preferably 75, and most preferably at least 100 contiguous amino acids of a CDK9. In further preferred embodiments, the fragment comprises the entire functionally active domain.

The term "CDK9 nucleic acid" refers to a DNA or RNA molecule that encodes a CDK9 polypeptide. Preferably, the CDK9 polypeptide or nucleic acid or fragment thereof is from a human, but can also be an ortholog, or derivative thereof with at least 70% sequence identity, preferably at least 80%, more preferably 85%, still more preferably 90%, and most preferably at least 95% sequence identity with human CDK9. Methods of identifying orthlogs are known in the art. Normally, orthologs in different species retain the same function, due to presence of one or more protein motifs and/or 3-dimensional structures. Orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen M A and Bork P, Proc Natl Acad Sci (1998) 95:5849-5856; Huynen M A et al., Genome Research (2000) 10: 1204-1210). Programs for multiple sequence alignment, such as CLUSTAL (Thompson J D et al, 1994, Nucleic Acids Res 22:4673-4680) may be used to highlight conserved regions and/or residues of orthologous proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. In evolution, when a gene duplication event follows speciation, a single gene in one species, such as *Drosophila*, may correspond to multiple genes (paralogs) in another, such as human. As used herein, the term "orthologs" encompasses paralogs. As used herein, "percent (%) sequence identity" with respect to a subject sequence, or a specified portion of a subject sequence, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1997) 215:403-410) with all the search parameters set to default values. The HSP S and HSP S2 parameters are dynamic values and are established by the program itself depending upon the composition of the particular sequence and composition of the particular database against which the sequence of interest is being searched. A % identity value is determined by the number of matching identical nucleotides or amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation.

A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Alternatively, an alignment for nucleic acid sequences is provided by the local homology algorithm of Smith and Waterman (Smith and Waterman, 1981, Advances in Applied Mathematics 2:482-489; database: European Bioinformatics Institute; Smith and Waterman, 1981, J. of Molec. Biol., 147:195-197; Nicholas et al., 1998, "A Tutorial on Searching Sequence Databases and Sequence Scoring Methods" (www.psc.edu) and references cited therein; W. R. Pearson, 1991, Genomics 11:635-650). This algorithm can be applied to amino acid sequences by using the scoring matrix developed by Dayhoff (Dayhoff: Atlas of Protein Sequences and Structure, M. O. Dayhoff ed., 5 suppl. 3:353-358, National Biomedical Research Foundation, Washington, D.C., USA), and normalized by Gribskov (Gribskov 1986 Nucl. Acids Res. 14(6):6745-6763). The Smith-Waterman algorithm may be employed where default parameters are used for scoring (for example, gap open penalty of 12, gap extension penalty of two). From the data generated, the "Match" value reflects "sequence identity."

Derivative nucleic acid molecules of the subject nucleic acid molecules include sequences that hybridize to the nucleic acid sequence of a CDK9. The stringency of hybridization can be controlled by temperature, ionic strength, pH, and the presence of denaturing agents such as formamide during hybridization and washing. Conditions routinely used are set out in readily available procedure texts (e.g., Current Protocol in Molecular Biology, Vol. 1, Chap. 2.10, John Wiley & Sons, Publishers (1994); Sambrook et al., Molecular Cloning, Cold Spring Harbor (1989)). In some embodiments, a nucleic acid molecule of the invention is capable of hybridizing to a nucleic acid molecule containing the nucleotide sequence of a CDK9 under high stringency hybridization conditions that are: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5×Denhardt's solution, 0.05% sodium pyrophosphate and 100 µg/ml herring sperm DNA; hybridization for 18-20 hours at 65° C. in a solution containing 6×SSC, 1×Denhardt's solution, 100 µg/ml yeast tRNA and 0.05% sodium pyrophosphate; and washing of filters at 65° C. for 1 h in a solution containing 0.1×SSC and 0.1% SDS (sodium dodecyl sulfate).

In other embodiments, moderately stringent hybridization conditions are used that are: pretreatment of filters containing nucleic acid for 6 h at 40° C. in a solution containing 35% formamide, 5×SSC, 50 mM Tris-HCl (pH7.5), 5 mM EDTA, 0.1% PVP, 0.1% Ficoll, 1% BSA, and 500 µg/ml denatured salmon sperm DNA; hybridization for 18-20 h at 40° C. in a solution containing 35% formamide, 5×SSC, 50 mM Tris-HCl (pH7.5), 5 mM EDTA, 0.02% PVP, 0.02% Ficoll, 0.2% BSA, 100 µg/ml salmon sperm DNA, and 10% (wt/vol) dextran sulfate; followed by washing twice for 1 hour at 55° C. in a solution containing 2×SSC and 0.1% SDS.

Alternatively, low stringency conditions can be used that are: incubation for 8 hours to overnight at 37° C. in a solution comprising 20% formamide, 5×SSC, 50 mM sodium phosphate (pH 7.6), 5×Denhardt's solution, 10% dextran sulfate, and 20 µg/ml denatured sheared salmon sperm DNA; hybridization in the same buffer for 18 to 20 hours; and washing of filters in 1×SSC at about 37° C. for 1 hour.

Isolation, Production, Expression, and Mis-Expression of CDK9 Nucleic Acids and Polypeptides CDK9 nucleic acids and polypeptides are useful for identifying and testing agents that modulate CDK9 function and for other applications related to the involvement of CDK9 in the IGF pathway. CDK9 nucleic acids and derivatives and orthologs thereof may be obtained using any available method. For instance, techniques for isolating cDNA or genomic DNA sequences of interest by screening DNA libraries or by using polymerase chain reaction (PCR) are well known in the art. In general, the particular use for the protein will dictate the particulars of expression, production, and purification methods. For instance, production of proteins for use in screening for modulating agents may require methods that preserve specific biological activities of these proteins, whereas production of proteins for antibody generation may require structural integrity of particular epitopes. Expression of proteins to be purified for screening or antibody production may require the addition of specific tags (e.g., generation of fusion proteins). Overexpression of a CDK9 protein for assays used to assess CDK9 function, such as involvement in cell cycle regulation or hypoxic response, may require expression in eukaryotic cell lines capable of these cellular activities. Techniques for the expression, production, and purification of proteins are well known in the art; any suitable means therefore may be used (e.g., Higgins S J and Hames B D (eds.) Protein Expression: A Practical Approach, Oxford University Press Inc., New York 1999; Stanbury P F et al., Principles of Fermentation Technology, $2^{nd}$ edition, Elsevier Science, New York, 1995; Doonan S (ed.) Protein Purification Protocols, Humana Press, New Jersey, 1996; Coligan J E et al, Current Protocols in Protein Science (eds.), 1999, John Wiley & Sons, New York). In particular embodiments, recombinant CDK9 is expressed in a cell line known to have defective IGF function. The recombinant cells are used in cell-based screening assay systems of the invention, as described further below.

The nucleotide sequence encoding a CDK9 polypeptide can be inserted into any appropriate expression vector. The necessary transcriptional and translational signals, including promoter/enhancer element, can derive from the native CDK9 gene and/or its flanking regions or can be heterologous. A variety of host-vector expression systems may be utilized, such as mammalian cell systems infected with virus (e.g. vaccinia virus, adenovirus, etc.); insect cell systems infected with virus (e.g. baculovirus); microorganisms such as yeast containing yeast vectors, or bacteria transformed with bacteriophage, plasmid, or cosmid DNA. An isolated host cell strain that modulates the expression of, modifies, and/or specifically processes the gene product may be used.

To detect expression of the CDK9 gene product, the expression vector can comprise a promoter operably linked to a CDK9 gene nucleic acid, one or more origins of replication, and, one or more selectable markers (e.g. thymidine kinase activity, resistance to antibiotics, etc.). Alternatively, recombinant expression vectors can be identified by assaying for the expression of the CDK9 gene product based on the physical or functional properties of the CDK9 protein in in vitro assay systems (e.g. immunoassays).

The CDK9 protein, fragment, or derivative may be optionally expressed as a fusion, or chimeric protein product (i.e. it is joined via a peptide bond to a heterologous protein sequence of a different protein), for example to facilitate purification or detection. A chimeric product can be made by ligating the appropriate nucleic acid sequences encoding the desired amino acid sequences to each other using standard methods and expressing the chimeric product. A chimeric product may also be made by protein synthetic techniques, e.g. by use of a peptide synthesizer (Hunkapiller et al., Nature (1984) 310:105-111).

Once a recombinant cell that expresses the CDK9 gene sequence is identified, the gene product can be isolated and purified using standard methods (e.g. ion exchange, affinity, and gel exclusion chromatography; centrifugation; differential solubility; electrophoresis). Alternatively, native CDK9 proteins can be purified from natural sources, by standard methods (e.g. immunoaffinity purification). Once a protein is obtained, it may be quantified and its activity measured by appropriate methods, such as immunoassay, bioassay, or other measurements of physical properties, such as crystallography.

The methods of this invention may also use cells that have been engineered for altered expression (mis-expression) of CDK9 or other genes associated with the IGF pathway. As used herein, mis-expression encompasses ectopic expression, over-expression, under-expression, and non-expression (e.g. by gene knock-out or blocking expression that would otherwise normally occur).

Genetically Modified Animals

Animal models that have been genetically modified to alter CDK9 expression may be used in in vivo assays to test for activity of a candidate IGF modulating agent, or to further assess the role of CDK9 in a IGF pathway process such as apoptosis or cell proliferation. Preferably, the altered CDK9 expression results in a detectable phenotype, such as decreased or increased levels of cell proliferation, angiogenesis, or apoptosis compared to control animals having normal CDK9 expression. The genetically modified animal may additionally have altered IGF expression (e.g. IGF knockout). Preferred genetically modified animals are mammals such as primates, rodents (preferably mice or rats), among others. Preferred non-mammalian species include zebrafish, *C. elegans*, and *Drosophila*. Preferred genetically modified animals are transgenic animals having a heterologous nucleic acid sequence present as an extrachromosomal element in a portion of its cells, i.e. mosaic animals (see, for example, techniques described by Jakobovits, 1994, Curr. Biol. 4:761-763.), or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal.

Methods of making transgenic animals are well-known in the art (for transgenic mice see Brinster et al., Proc. Nat. Acad. Sci. USA 82: 4438-4442 (1985), U.S. Pat. Nos. 4,736,866 and 4,870,009, both by Leder et al., U.S. Pat. No. 4,873,191 by Wagner et al., and Hogan, B., Manipulating the Mouse Embryo, Cold Spring Harbor Laboratory Press, Cold Spring Harbor, N.Y., (1986); for particle bombardment see U.S. Pat. No. 4,945,050, by Sandford et al.; for transgenic *Drosophila* see Rubin and Spradling, Science (1982) 218:348-53 and U.S. Pat. No. 4,670,388; for transgenic insects see Berghammer A. J. et al., A Universal Marker for Transgenic Insects (1999) Nature 402:370-371; for transgenic Zebrafish see Lin S., Transgenic Zebrafish, Methods Mol Biol. (2000); 136: 375-3830); for microinjection procedures for fish, amphibian eggs and birds see Houdebine and Chourrout, Experientia (1991) 47:897-905; for transgenic rats see Hammer et al., Cell (1990) 63:1099-1112; and for culturing of embryonic stem (ES) cells and the subsequent production of transgenic animals by the introduction of DNA into ES cells using methods such as electroporation, calcium phosphate/DNA precipitation and direct injection see, e.g., Teratocarcinomas and Embryonic Stem Cells, A Practical Approach, E. J. Robertson, ed., IRL Press (1987)). Clones of the nonhuman transgenic animals can be produced according to available methods (see Wilmut, I. et al. (1997) Nature 385:810-813; and PCT International Publication Nos. WO 97/07668 and WO 97/07669).

In one embodiment, the transgenic animal is a "knock-out" animal having a heterozygous or homozygous alteration in the sequence of an endogenous CDK9 gene that results in a decrease of CDK9 function, preferably such that CDK9 expression is undetectable or insignificant. Knock-out animals are typically generated by homologous recombination with a vector comprising a transgene having at least a portion of the gene to be knocked out. Typically a deletion, addition or substitution has been introduced into the transgene to functionally disrupt it. The transgene can be a human gene (e.g., from a human genomic clone) but more preferably is an ortholog of the human gene derived from the transgenic host species. For example, a mouse CDK9 gene is used to construct a homologous recombination vector suitable for altering an endogenous CDK9 gene in the mouse genome. Detailed methodologies for homologous recombination in mice are available (see Capecchi, Science (1989) 244:1288-1292; Joyner et al., Nature (1989) 338:153-156). Procedures for the production of non-rodent transgenic mammals and other animals are also available (Houdebine and Chourrout, supra; Pursel et al., Science (1989) 244:1281-1288; Simms et al., Bio/Technology (1988) 6:179-183). In a preferred embodiment, knock-out animals, such as mice harboring a knockout of a specific gene, may be used to produce antibodies against the human counterpart of the gene that has been knocked out (Claesson M H et al., (1994) Scan J Immunol 40:257-264; Declerck P J et al., (1995) J Biol Chem. 270: 8397-400).

In another embodiment, the transgenic animal is a "knock-in" animal having an alteration in its genome that results in altered expression (e.g., increased (including ectopic) or decreased expression) of the CDK9 gene, e.g., by introduction of additional copies of CDK9, or by operatively inserting a regulatory sequence that provides for altered expression of an endogenous copy of the CDK9 gene. Such regulatory sequences include inducible, tissue-specific, and constitutive promoters and enhancer elements. The knock-in can be homozygous or heterozygous.

Transgenic nonhuman animals can also be produced that contain selected systems allowing for regulated expression of the transgene. One example of such a system that may be produced is the cre/loxP recombinase system of bacteriophage P1 (Lakso et al., PNAS (1992) 89:6232-6236; U.S. Pat. No. 4,959,317). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase. Another example of a recombinase system is the FLP recombinase system of Saccharomyces cerevisiae (O'Gorman et al. (1991) Science 251:1351-1355; U.S. Pat. No. 5,654,182). In a preferred embodiment, both Cre-LoxP and Flp-Frt are used in the same system to regulate expression of the transgene, and for sequential deletion of vector sequences in the same cell (Sun X et al (2000) Nat Genet 25:83-6).

The genetically modified animals can be used in genetic studies to further elucidate the IGF pathway, as animal models of disease and disorders implicating defective IGF function, and for in vivo testing of candidate therapeutic agents, such as those identified in screens described below. The candidate therapeutic agents are administered to a genetically modified animal having altered CDK9 function and phenotypic changes are compared with appropriate control animals such as genetically modified animals that receive placebo treatment, and/or animals with unaltered CDK9 expression that receive candidate therapeutic agent.

In addition to the above-described genetically modified animals having altered CDK9 function, animal models having defective IGF function (and otherwise normal CDK9 function), can be used in the methods of the present invention. For example, a mouse with defective PTEN function can be used to assess, in vivo, the activity of a candidate PTEN modulating agent identified in one of the in vitro assays described below. Transgenic mice with defective PTEN function have been described in literature (Di Cristofano et al, supra). Preferably, the candidate IGF modulating agent when administered to a model system with cells defective in IGF function, produces a detectable phenotypic change in the model system indicating that the IGF function is restored, i.e., the cells exhibit normal cell cycle progression.

Modulating Agents

The invention provides methods to identify agents that interact with and/or modulate the function of CDK9 and/or the IGF pathway. Modulating agents identified by the methods are also part of the invention. Such agents are useful in a variety of diagnostic and therapeutic applications associated with the IGF pathway, as well as in further analysis of the CDK9 protein and its contribution to the IGF pathway. Accordingly, the invention also provides methods for modulating the IGF pathway comprising the step of specifically modulating CDK9 activity by administering a CDK9-interacting or -modulating agent.

As used herein, a "CDK9-modulating agent" is any agent that modulates CDK9 function, for example, an agent that interacts with CDK9 to inhibit or enhance CDK9 activity or otherwise affect normal CDK9 function. CDK9 function can be affected at any level, including transcription, protein expression, protein localization, and cellular or extra-cellular activity. In a preferred embodiment, the CDK9-modulating agent specifically modulates the function of the CDK9. The phrases "specific modulating agent", "specifically modulates", etc., are used herein to refer to modulating agents that directly bind to the CDK9 polypeptide or nucleic acid, and preferably inhibit, enhance, or otherwise alter, the function of the CDK9. These phrases also encompass modulating agents that alter the interaction of the CDK9 with a binding partner, substrate, or cofactor (e.g. by binding to a binding partner of a CDK9, or to a protein/binding partner complex, and altering CDK9 function). In a further preferred embodiment, the CDK9-modulating agent is a modulator of the IGF pathway (e.g. it restores and/or upregulates IGF function) and thus is also a IGF-modulating agent.

Preferred CDK9-modulating agents include small molecule compounds; CDK9-interacting proteins, including antibodies and other biotherapeutics; and nucleic acid modulators such as antisense and RNA inhibitors. The modulating agents may be formulated in pharmaceutical compositions, for example, as compositions that may comprise other active ingredients, as in combination therapy, and/or suitable carriers or excipients. Techniques for formulation and administration of the compounds may be found in "Remington's Pharmaceutical Sciences" Mack Publishing Co., Easton, Pa., 19$^{th}$ edition.

Small Molecule Modulators

Small molecules are often preferred to modulate function of proteins with enzymatic function, and/or containing protein interaction domains. Chemical agents, referred to in the art as "small-molecule" compounds are typically organic, non-peptide molecules, having a molecular weight up to 10,000, preferably up to 5,000, more preferably up to 1,000, and most preferably up to 500 daltons. This class of modulators includes chemically synthesized molecules, for instance, compounds from combinatorial chemical libraries. Synthetic compounds may be rationally designed or identified based on known or inferred properties of the CDK9 protein or may be identified by screening compound libraries. Alternative appropriate modulators of this class are natural products, particularly secondary metabolites from organisms such as plants or fungi, which can also be identified by screening compound libraries for CDK9-modulating activity. Methods for generating and obtaining compounds are well known in the art (Schreiber S L, Science (2000) 151: 1964-1969; Radmann J and Gunther J, Science (2000) 151:1947-1948).

Small molecule modulators identified from screening assays, as described below, can be used as lead compounds from which candidate clinical compounds may be designed, optimized, and synthesized. Such clinical compounds may have utility in treating pathologies associated with the IGF pathway. The activity of candidate small molecule modulating agents may be improved several-fold through iterative secondary functional validation, as further described below, structure determination, and candidate modulator modification and testing. Additionally, candidate clinical compounds are generated with specific regard to clinical and pharmacological properties. For example, the reagents may be derivatized and re-screened using in vitro and in vivo assays to optimize activity and minimize toxicity for pharmaceutical development.

Protein Modulators

Specific CDK9-interacting proteins are useful in a variety of diagnostic and therapeutic applications related to the IGF pathway and related disorders, as well as in validation assays for other CDK9-modulating agents. In a preferred embodiment, CDK9-interacting proteins affect normal CDK9 function, including transcription, protein expression, protein localization, and cellular or extra-cellular activity. In another embodiment, CDK9-interacting proteins are useful in detecting and providing information about the function of CDK9 proteins, as is relevant to IGF related disorders, such as cancer (e.g., for diagnostic means).

A CDK9-interacting protein may be endogenous, i.e. one that naturally interacts genetically or biochemically with a CDK9, such as a member of the CDK9 pathway that modulates CDK9 expression, localization, and/or activity. CDK9-modulators include dominant negative forms of CDK9-interacting proteins and of CDK9 proteins themselves. Yeast two-hybrid and variant screens offer preferred methods for identifying endogenous CDK9-interacting proteins (Finley, R. L. et al. (1996) in DNA Cloning-Expression Systems: A Practical Approach, eds. Glover D. & Hames B. D (Oxford University Press, Oxford, England), pp. 169-203; Fashema S F et al., Gene (2000) 250:1-14; Drees B L Curr Opin Chem Biol (1999) 3:64-70; Vidal M and Legrain P Nucleic Acids Res (1999) 27:919-29; and U.S. Pat. No. 5,928,868). Mass spectrometry is an alternative preferred method for the elucidation of protein complexes (reviewed in, e.g., Pandley A and Mann M, Nature (2000) 405:837-846; Yates JR 3$^{rd}$, Trends Genet (2000) 16:5-8).

A CDK9-interacting protein may be an exogenous protein, such as a CDK9-specific antibody or a T-cell antigen receptor (see, e.g., Harlow and Lane (1988) Antibodies, A Laboratory Manual, Cold Spring Harbor Laboratory; Harlow and Lane (1999) Using antibodies: a laboratory manual. Cold Spring Harbor, N.Y.: Cold Spring Harbor Laboratory Press). CDK9 antibodies are further discussed below.

In preferred embodiments, a CDK9-interacting protein specifically binds a CDK9 protein. In alternative preferred embodiments, a CDK9-modulating agent binds a CDK9 substrate, binding partner, or cofactor.

Antibodies

In another embodiment, the protein modulator is a CDK9 specific antibody agonist or antagonist. The antibodies have therapeutic and diagnostic utilities, and can be used in screening assays to identify CDK9 modulators. The antibodies can also be used in dissecting the portions of the CDK9 pathway responsible for various cellular responses and in the general processing and maturation of the CDK9.

Antibodies that specifically bind CDK9 polypeptides can be generated using known methods. Preferably the antibody is specific to a mammalian ortholog of CDK9 polypeptide, and more preferably, to human CDK9. Antibodies may be polyclonal, monoclonal (mAbs), humanized or chimeric antibodies, single chain antibodies, Fab fragments, F(ab').sub.2 fragments, fragments produced by a FAb expression library, anti-idiotypic (anti-Id) antibodies, and epitope-binding fragments of any of the above. Epitopes of CDK9 which are particularly antigenic can be selected, for example, by routine screening of CDK9 polypeptides for antigenicity or by applying a theoretical method for selecting antigenic regions of a protein (Hopp and Wood (1981), Proc. Natl. Acad. Sci. U.S.A. 78:3824-28; Hopp and Wood, (1983) Mol. Immunol. 20:483-89; Sutcliffe et al., (1983) Science 219:660-66) to the amino acid sequence of a CDK9. Monoclonal antibodies with affinities of $10^8$ $M^{-1}$ preferably $10^9$ $M^{-1}$ to $10^{10}$ $M^{-1}$, or stronger can be made by standard procedures as described (Harlow and Lane, supra; Goding (1986) Monoclonal Antibodies: Principles and Practice (2d ed) Academic Press, New York; and U.S. Pat. Nos. 4,381,292; 4,451,570; and 4,618,577). Antibodies may be generated against crude cell extracts of CDK9 or substantially purified fragments thereof. If CDK9 fragments are used, they preferably comprise at least 10, and more preferably, at least 20 contiguous amino acids of a CDK9 protein. In a particular embodiment, CDK9-specific antigens and/or immunogens are coupled to carrier proteins that stimulate the immune response. For example, the subject polypeptides are covalently coupled to the keyhole limpet hemocyanin (KLH) carrier, and the conjugate is emulsified in Freund's complete adjuvant, which enhances the immune response. An appropriate immune system such as a laboratory rabbit or mouse is immunized according to conventional protocols.

The presence of CDK9-specific antibodies is assayed by an appropriate assay such as a solid phase enzyme-linked immunosorbant assay (ELISA) using immobilized corresponding CDK9 polypeptides. Other assays, such as radioimmunoassays or fluorescent assays might also be used.

Chimeric antibodies specific to CDK9 polypeptides can be made that contain different portions from different animal species. For instance, a human immunoglobulin constant region may be linked to a variable region of a murine mAb, such that the antibody derives its biological activity from the human antibody, and its binding specificity from the murine fragment. Chimeric antibodies are produced by splicing together genes that encode the appropriate regions from each species (Morrison et al., Proc. Natl. Acad. Sci. (1984) 81:6851-6855; Neuberger et al., Nature (1984) 312:604-608; Takeda et al., Nature (1985) 31:452-454). Humanized antibodies, which are a form of chimeric antibodies, can be generated by grafting complementary-determining regions (CDRs) (Carlos, T. M., J. M. Harlan. 1994. Blood 84:2068-2101) of mouse antibodies into a background of human framework regions and constant regions by recombinant DNA technology (Riechmann L M, et al., 1988 Nature 323: 323-327). Humanized antibodies contain ~10% murine sequences and ~90% human sequences, and thus further reduce or eliminate immunogenicity, while retaining the antibody specificities (Co M S, and Queen C. 1991 Nature 351: 501-501; Morrison S L., 1992 Ann. Rev. Immun. 10:239-265). Humanized antibodies and methods of their production are well-known in the art (U.S. Pat. Nos. 5,530,101, 5,585,089, 5,693,762, and 6,180,370).

CDK9-specific single chain antibodies which are recombinant, single chain polypeptides formed by linking the heavy and light chain fragments of the Fv regions via an amino acid bridge, can be produced by methods known in the art (U.S. Pat. No. 4,946,778; Bird, Science (1988) 242:423-426; Huston et al., Proc. Natl. Acad. Sci. USA (1988) 85:5879-5883; and Ward et al., Nature (1989) 334:544-546).

Other suitable techniques for antibody production involve in vitro exposure of lymphocytes to the antigenic polypeptides or alternatively to selection of libraries of antibodies in phage or similar vectors (Huse et al., Science (1989) 246: 1275-1281). As used herein, T-cell antigen receptors are included within the scope of antibody modulators (Harlow and Lane, 1988, supra).

The polypeptides and antibodies of the present invention may be used with or without modification. Frequently, antibodies will be labeled by joining, either covalently or non-covalently, a substance that provides for a detectable signal, or that is toxic to cells that express the targeted protein (Menard S, et al., Int J. Biol Markers (1989) 4:131-134). A wide variety of labels and conjugation techniques are known and are reported extensively in both the scientific and patent literature. Suitable labels include radionuclides, enzymes, substrates, cofactors, inhibitors, fluorescent moieties, fluorescent emitting lanthanide metals, chemiluminescent moieties, bioluminescent moieties, magnetic particles, and the like (U.S. Pat. Nos. 3,817,837; 3,850,752; 3,939,350; 3,996,345; 4,277,437; 4,275,149; and 4,366,241). Also, recombinant immunoglobulins may be produced (U.S. Pat. No. 4,816,567). Antibodies to cytoplasmic polypeptides may be delivered and reach their targets by conjugation with membrane-penetrating toxin proteins (U.S. Pat. No. 6,086,900).

When used therapeutically in a patient, the antibodies of the subject invention are typically administered parenterally, when possible at the target site, or intravenously. The therapeutically effective dose and dosage regimen is determined by clinical studies. Typically, the amount of antibody administered is in the range of about 0.1 mg/kg-to about 10 mg/kg of patient weight. For parenteral administration, the antibodies are formulated in a unit dosage injectable form (e.g., solution, suspension, emulsion) in association with a pharmaceutically acceptable vehicle. Such vehicles are inherently nontoxic and non-therapeutic. Examples are water, saline, Ringer's solution, dextrose solution, and 5% human serum albumin. Nonaqueous vehicles such as fixed oils, ethyl oleate, or liposome carriers may also be used. The vehicle may contain minor amounts of additives, such as buffers and preservatives, which enhance isotonicity and chemical stability or otherwise enhance therapeutic potential. The antibodies' concentrations in such vehicles are typically in the range of about 1 mg/ml to about 10 mg/ml. Immunotherapeutic methods are further described in the literature (U.S. Pat. No. 5,859,206; WO0073469).

Nucleic Acid Modulators

Other preferred CDK9-modulating agents comprise nucleic acid molecules, such as antisense oligomers or double stranded RNA (dsRNA), which generally inhibit CDK9 activity. Preferred nucleic acid modulators interfere with the function of the CDK9 nucleic acid such as DNA replication, transcription, translocation of the CDK9 RNA to the site of protein translation, translation of protein from the CDK9 RNA, splicing of the CDK9 RNA to yield one or more mRNA species, or catalytic activity which may be engaged in or facilitated by the CDK9 RNA.

In one embodiment, the antisense oligomer is an oligonucleotide that is sufficiently complementary to a CDK9 mRNA to bind to and prevent translation, preferably by binding to the 5' untranslated region. CDK9-specific antisense oligonucleotides, preferably range from at least 6 to about 200 nucleotides. In some embodiments the oligonucleotide is preferably at least 10, 15, or 20 nucleotides in length. In other embodiments, the oligonucleotide is preferably less than 50, 40, or 30 nucleotides in length. The oligonucleotide can be DNA or RNA or a chimeric mixture or derivatives or modified versions thereof, single-stranded or double-stranded. The oligonucleotide can be modified at the base moiety, sugar moiety, or phosphate backbone. The oligonucleotide may include other appending groups such as peptides, agents that facilitate transport across the cell membrane, hybridization-triggered cleavage agents, and intercalating agents.

In another embodiment, the antisense oligomer is a phosphothioate morpholino oligomer (PMO). PMOs are assembled from four different morpholino subunits, each of which contain one of four genetic bases (A, C, G, or T) linked to a six-membered morpholine ring. Polymers of these subunits are joined by non-ionic phosphodiamidate intersubunit linkages. Details of how to make and use PMOs and other antisense oligomers are well known in the art (e.g. see WO99/18193; Probst J C, Antisense Oligodeoxynucleotide and Ribozyme Design, Methods. (2000) 22(3):271-281; Summerton J, and Weller D. 1997 Antisense Nucleic Acid Drug Dev.: 7:187-95; U.S. Pat. No. 5,235,033; and U.S. Pat. No. 5,378,841).

Alternative preferred CDK9 nucleic acid modulators are double-stranded RNA species mediating RNA interference (RNAi). RNAi is the process of sequence-specific, post-transcriptional gene silencing in animals and plants, initiated by double-stranded RNA (dsRNA) that is homologous in sequence to the silenced gene. Methods relating to the use of RNAi to silence genes in *C. elegans, Drosophila*, plants, and humans are known in the art (Fire A, et al., 1998 Nature 391:806-811; Fire, A. Trends Genet. 15, 358-363 (1999); Sharp, P. A. RNA interference 2001. Genes Dev. 15, 485-490 (2001); Hammond, S. M., et al., Nature Rev. Genet. 2, 110-1119 (2001); Tuschl, T. Chem. Biochem. 2, 239-245 (2001); Hamilton, A. et al., Science 286, 950-952 (1999); Hammond, S. M., et al., Nature 404, 293-296 (2000); Zamore, P. D., et al., Cell 101, 25-33 (2000); Bernstein, E., et al., Nature 409, 363-366 (2001); Elbashir, S. M., et al., Genes Dev. 15, 188-200 (2001); WO0129058; WO9932619; Elbashir S M, et al., 2001 Nature 411:494-498; Novina C D and Sharp P. 2004 Nature 430:161-164; Soutschek J et al 2004 Nature 432:173-178; Hsieh A C et al. (2004) NAR 32(3):893-901).

Nucleic acid modulators are commonly used as research reagents, diagnostics, and therapeutics. For example, antisense oligonucleotides, which are able to inhibit gene expression with exquisite specificity, are often used to elucidate the function of particular genes (see, for example, U.S. Pat. No. 6,165,790). Nucleic acid modulators are also used, for example, to distinguish between functions of various members of a biological pathway. For example, antisense oligomers have been employed as therapeutic moieties in the treatment of disease states in animals and man and have been demonstrated in numerous clinical trials to be safe and effective (Milligan J F, et al, Current Concepts in Antisense Drug Design, J Med Chem. (1993) 36:1923-1937; Tonkinson J L et al., Antisense Oligodeoxynucleotides as Clinical Therapeutic Agents, Cancer Invest. (1996) 14:54-65). Accordingly, in one aspect of the invention, a CDK9-specific nucleic acid modulator is used in an assay to further elucidate the role of the CDK9 in the IGF pathway, and/or its relationship to other members of the pathway. In another aspect of the invention, a CDK9-specific antisense oligomer is used as a therapeutic agent for treatment of IGF-related disease states.

Assay Systems

The invention provides assay systems and screening methods for identifying specific modulators of CDK9 activity. As used herein, an "assay system" encompasses all the components required for performing and analyzing results of an assay that detects and/or measures a particular event. In general, primary assays are used to identify or confirm a modulator's specific biochemical or molecular effect with respect to the CDK9 nucleic acid or protein. In general, secondary assays further assess the activity of a CDK9 modulating agent identified by a primary assay and may confirm that the modulating agent affects CDK9 in a manner relevant to the IGF pathway. In some cases, CDK9 modulators will be directly tested in a secondary assay.

In a preferred embodiment, the screening method comprises contacting a suitable assay system comprising a CDK9 polypeptide or nucleic acid with a candidate agent under conditions whereby, but for the presence of the agent, the system provides a reference activity (e.g. kinase activity), which is based on the particular molecular event the screening method detects. A statistically significant difference between the agent-biased activity and the reference activity indicates that the candidate agent modulates CDK9 activity, and hence the IGF pathway. The CDK9 polypeptide or nucleic acid used in the assay may comprise any of the nucleic acids or polypeptides described above.

Primary Assays

The type of modulator tested generally determines the type of primary assay.

Primary Assays for Small Molecule Modulators

For small molecule modulators, screening assays are used to identify candidate modulators. Screening assays may be cell-based or may use a cell-free system that recreates or retains the relevant biochemical reaction of the target protein (reviewed in Sittampalam G S et al., Curr Opin Chem Biol (1997) 1:384-91 and accompanying references). As used herein the term "cell-based" refers to assays using live cells, dead cells, or a particular cellular fraction, such as a membrane, endoplasmic reticulum, or mitochondrial fraction. The term "cell free" encompasses assays using substantially purified protein (either endogenous or recombinantly produced), partially purified or crude cellular extracts. Screening assays may detect a variety of molecular events, including protein-DNA interactions, protein-protein interactions (e.g., receptor-ligand binding), transcriptional activity (e.g., using a reporter gene), enzymatic activity (e.g., via a property of the substrate), activity of second messengers, immunogenicty and changes in cellular morphology or other cellular characteristics. Appropriate screening assays may use a wide range of detection methods including fluorescent, radioactive, colorimetric, spectrophotometric, and amperometric methods, to provide a read-out for the particular molecular event detected.

Cell-based screening assays usually require systems for recombinant expression of CDK9 and any auxiliary proteins demanded by the particular assay. Appropriate methods for generating recombinant proteins produce sufficient quantities of proteins that retain their relevant biological activities and are of sufficient purity to optimize activity and assure assay reproducibility. Yeast two-hybrid and variant screens, and mass spectrometry provide preferred methods for determining protein-protein interactions and elucidation of protein complexes. In certain applications, when CDK9-interacting proteins are used in screens to identify small molecule modulators, the binding specificity of the interacting protein to the CDK9 protein may be assayed by various known methods such as substrate processing (e.g. ability of the candidate CDK9-specific binding agents to function as negative effectors in CDK9-expressing cells), binding equilibrium constants (usually at least about $10^7 M^{-1}$, preferably at least about $10^8 M^{-1}$, more preferably at least about $10^9 M^{-1}$), and immunogenicity (e.g. ability to elicit CDK9 specific antibody in a heterologous host such as a mouse, rat, goat or rabbit). For enzymes and receptors, binding may be assayed by, respectively, substrate and ligand processing.

The screening assay may measure a candidate agent's ability to specifically bind to or modulate activity of a CDK9 polypeptide, a fusion protein thereof, or to cells or membranes bearing the polypeptide or fusion protein. The CDK9 polypeptide can be full length or a fragment thereof that retains functional CDK9 activity. The CDK9 polypeptide may be fused to another polypeptide, such as a peptide tag for detection or anchoring, or to another tag. The CDK9 polypeptide is preferably human CDK9, or is an ortholog or derivative thereof as described above. In a preferred embodiment, the screening assay detects candidate agent-based modulation of CDK9 interaction with a binding target, such as an endogenous or exogenous protein or other substrate that has CDK9-specific binding activity, and can be used to assess normal CDK9 gene function.

Suitable assay formats that may be adapted to screen for CDK9 modulators are known in the art. Preferred screening assays are high throughput or ultra high throughput and thus provide automated, cost-effective means of screening compound libraries for lead compounds (Fernandes P B, Curr Opin Chem Biol (1998) 2:597-603; Sundberg S A, Curr Opin Biotechnol 2000, 11:47-53). In one preferred embodiment, screening assays uses fluorescence technologies, including fluorescence polarization, time-resolved fluorescence, and fluorescence resonance energy transfer. These systems offer means to monitor protein-protein or DNA-protein interactions in which the intensity of the signal emitted from dye-labeled molecules depends upon their interactions with partner molecules (e.g., Selvin P R, Nat Struct Biol (2000) 7:730-4; Fernandes P B, supra; Hertzberg R P and Pope A J, Curr Opin Chem Biol (2000) 4:445-451).

A variety of suitable assay systems may be used to identify candidate CDK9 and IGF pathway modulators (e.g. U.S. Pat. No. 6,165,992 and U.S. Pat. No. 6,720,162 (kinase assays); U.S. Pat. Nos. 5,550,019 and 6,133,437 (apoptosis assays); and U.S. Pat. Nos. 5,976,782, 6,225,118 and 6,444,434 (angiogenesis assays), among others). Specific preferred assays are described in more detail below.

Protein kinases, key signal transduction proteins that may be either membrane-associated or intracellular, catalyze the transfer of gamma phosphate from adenosine triphosphate (ATP) to a serine, threonine or tyrosine residue in a protein substrate. Radioassays, which monitor the transfer from [gamma-$^{32}$P or -$^{33}$P]ATP, are frequently used to assay kinase activity. For instance, a scintillation assay for p56 (lck) kinase activity monitors the transfer of the gamma phosphate from [gamma-$^{33}$P] ATP to a biotinylated peptide substrate. The substrate is captured on a streptavidin coated bead that transmits the signal (Beveridge M et al., J Biomol Screen (2000) 5:205-212). This assay uses the scintillation proximity assay (SPA), in which only radio-ligand bound to receptors tethered to the surface of an SPA bead are detected by the scintillant immobilized within it, allowing binding to be measured without separation of bound from free ligand. Other assays for protein kinase activity may use antibodies that specifically recognize phosphorylated substrates. For instance, the kinase receptor activation (KIRA) assay measures receptor tyrosine kinase activity by ligand stimulating the intact receptor in cultured cells, then capturing solubilized receptor with specific antibodies and quantifying phosphorylation via phosphotyrosine ELI S A (Sadick M D, Dev Biol Stand (1999) 97:121-133). Another example of antibody based assays for protein kinase activity is TRF (time-resolved fluorometry). This method utilizes europium chelate-labeled anti-phosphotyrosine antibodies to detect phosphate transfer to a polymeric substrate coated onto microtiter plate wells. The amount of phosphorylation is then detected using time-resolved, dissociation-enhanced fluorescence (Braunwalder A F, et al., Anal Biochem 1996 Jul. 1; 238(2):159-64). Yet other assays for kinases involve uncoupled, pH sensitive assays that can be used for high-throughput screening of potential inhibitors or for determining substrate specificity. Since kinases catalyze the transfer of a gamma-phosphoryl group from ATP to an appropriate hydroxyl acceptor with the release of a proton, a pH sensitive assay is based on the detection of this proton using an appropriately matched buffer/indicator system (Chapman E and Wong C H (2002) Bioorg Med Chem. 10:551-5).

Apoptosis Assays.

Apoptosis or programmed cell death is a suicide program is activated within the cell, leading to fragmentation of DNA, shrinkage of the cytoplasm, membrane changes and cell death. Apoptosis is mediated by proteolytic enzymes of the caspase family. Many of the altering parameters of a cell are measurable during apoptosis. Assays for apoptosis may be performed by terminal deoxynucleotidyl transferase-mediated digoxigenin-11-dUTP nick end labeling (TUNEL) assay. The TUNEL assay is used to measure nuclear DNA fragmentation characteristic of apoptosis (Lazebnik et al., 1994, Nature 371, 346), by following the incorporation of fluorescein-dUTP (Yonehara et al., 1989, J. Exp. Med. 169, 1747). Apoptosis may further be assayed by acridine orange staining of tissue culture cells (Lucas, R., et al., 1998, Blood 15:4730-41). Other cell-based apoptosis assays include the caspase-3/7 assay and the cell death nucleosome ELISA assay. The caspase 3/7 assay is based on the activation of the caspase cleavage activity as part of a cascade of events that occur during programmed cell death in many apoptotic pathways. In the caspase 3/7 assay (commercially available Apo-ONE™ Homogeneous Caspase-3/7 assay from Promega, cat#67790), lysis buffer and caspase substrate are mixed and added to cells. The caspase substrate becomes fluorescent when cleaved by active caspase 3/7. The nucleosome ELISA assay is a general cell death assay known to those skilled in the art, and available commercially (Roche, Cat#1774425). This assay is a quantitative sandwich-enzyme-immunoassay which uses monoclonal antibodies directed against DNA and histones respectively, thus specifically determining amount of mono- and oligonucleosomes in the cytoplasmic fraction of cell lysates. Mono and oligonucleosomes are enriched in the cytoplasm during apoptosis due to the fact that DNA fragmentation occurs several hours before the plasma membrane breaks down, allowing for accumalation in the cytoplasm. Nucleosomes are not present in the cytoplasmic fraction of cells that are not undergoing apoptosis. The Phospho-histone H2B assay is another apoptosis assay, based on phosphorylation of histone H2B as a result of apoptosis. Fluorescent dyes that are associated with phosphohistone H2B may be used to measure the increase of phosphohistone H2B as a result of apoptosis. Apoptosis assays that simultaneously measure multiple parameters associated with apoptosis have also been developed. In such assays, various cellular parameters that can be associated with antibodies or fluorescent dyes, and that mark various stages of apoptosis are labeled, and the results are measured using instruments such as Cellomics™ ArrayScan® HCS System. The measurable parameters and their markers include anti-active caspase-3 antibody which marks intermediate stage apoptosis, anti-PARP-p85 antibody (cleaved PARP) which marks late stage apoptosis, Hoechst labels which label the nucleus and are used to measure nuclear swelling as a measure of early apoptosis and nuclear condensation as a measure of late apoptosis, TOTO-3 fluorescent dye which labels DNA of dead cells with high cell membrane permeability, and anti-alpha-tubulin or F-actin labels, which assess cytoskeletal changes in cells and correlate well with TOTO-3 label.

An apoptosis assay system may comprise a cell that expresses a CDK9, and that optionally has defective IGF function (e.g. IGF is over-expressed or under-expressed relative to wild-type cells). A test agent can be added to the apoptosis assay system and changes in induction of apoptosis relative to controls where no test agent is added, identify candidate IGF modulating agents. In some embodiments of the invention, an apoptosis assay may be used as a secondary assay to test a candidate IGF modulating agents that is initially identified using a cell-free assay system. An apoptosis assay may also be used to test whether CDK9 function plays a direct role in apoptosis. For example, an apoptosis assay may be performed on cells that over- or under-express CDK9 relative to wild type cells. Differences in apoptotic response compared to wild type cells suggests that the CDK9 plays a direct role in the apoptotic response. Apoptosis assays are described further in U.S. Pat. No. 6,133,437.

Cell Proliferation and Cell Cycle Assays.

Cell proliferation may be assayed via bromodeoxyuridine (BRDU) incorporation. This assay identifies a cell population undergoing DNA synthesis by incorporation of BRDU into newly-synthesized DNA. Newly-synthesized DNA may then be detected using an anti-BRDU antibody (Hoshino et al., 1986, Int. J. Cancer 38, 369; Campana et al., 1988, J. Immunol. Meth. 107, 79), or by other means.

Cell proliferation is also assayed via phospho-histone H3 staining, which identifies a cell population undergoing mitosis by phosphorylation of histone H3. Phosphorylation of histone H3 at serine 10 is detected using an antibody specfic to the phosphorylated form of the serine 10 residue of histone H3. (Chadlee, D. N. 1995, J. Biol. Chem 270:20098-105). Cell Proliferation may also be examined using [$^3$H]-thymidine incorporation (Chen, J., 1996, Oncogene 13:1395-403; Jeoung, J., 1995, J. Biol. Chem. 270:18367-73). This assay allows for quantitative characterization of S-phase DNA syntheses. In this assay, cells synthesizing DNA will incorporate [$^3$H]-thymidine into newly synthesized DNA. Incorporation can then be measured by standard techniques such as by counting of radioisotope in a scintillation counter (e.g., Beckman LS 3800 Liquid Scintillation Counter). Another proliferation assay uses the dye Alamar Blue (available from Biosource International), which fluoresces when reduced in living cells and provides an indirect measurement of cell number (Voytik-Harbin S L et al., 1998, In Vitro Cell Dev Biol Anim 34:239-46). Yet another proliferation assay, the MTS assay, is based on in vitro cytotoxicity assessment of industrial chemicals, and uses the soluble tetrazolium salt, MTS. MTS assays are commercially available, for example, the Promega CellTiter 96® AQueous Non-Radioactive Cell Proliferation Assay (Cat.# G5421).

Cell proliferation may also be assayed by colony formation in soft agar, or clonogenic survival assay (Sambrook et al., Molecular Cloning, Cold Spring Harbor (1989)). For example, cells transformed with CDK9 are seeded in soft agar plates, and colonies are measured and counted after two weeks incubation.

Cell proliferation may also be assayed by measuring ATP levels as indicator of metabolically active cells. Such assays are commercially available, for example Cell Titer-Glo™, which is a luminescent homogeneous assay available from Promega.

Involvement of a gene in the cell cycle may be assayed by flow cytometry (Gray J W et al. (1986) Int J Radiat Biol Relat Stud Phys Chem Med 49:237-55). Cells transfected with a CDK9 may be stained with propidium iodide and evaluated in a flow cytometer (available from Becton Dickinson), which indicates accumulation of cells in different stages of the cell cycle.

Involvement of a gene in cell cycle may also be assayed by FOXO nuclear translocation assays. The FOXO family of transcription factors are mediators of various cellular functions including cell cycle progression and cell death, and are negatively regulated by activation of the PI3 kinase pathway. Akt phosphorylation of FOXO family members leads to FOXO sequestration in the cytoplasm and transcriptional inactivation (Medema, R. H et al (2000) Nature 404: 782-787). PTEN is a negative regulator of PI3 kinase pathway. Activation of PTEN, or loss of P13 kinase or AKT, prevents phosphorylation of FOXO, leading to accumulation of FOXO in the nucleus, transcriptional activation of FOXO regulated genes, and apoptosis. Alternatively, loss of PTEN leads to pathway activation and cell survival (Nakamura, N. et al (2000) Mol Cell Biol 20: 8969-8982). FOXO translocation into the cytoplasm is used in assays and screens to identify members and/or modulators of the PTEN pathway. FOXO translocation assays using GFP or luciferase as detection reagents are known in the art (e.g., Zhang X et al (2002) J Biol Chem 277:45276-45284; and Li et al (2003) Mol Cell Biol 23:104-118).

Accordingly, a cell proliferation or cell cycle assay system may comprise a cell that expresses a CDK9, and that optionally has defective IGF function (e.g. IGF is over-expressed or under-expressed relative to wild-type cells). A test agent can be added to the assay system and changes in cell proliferation or cell cycle relative to controls where no test agent is added, identify candidate IGF modulating agents. In some embodiments of the invention, the cell proliferation or cell cycle assay may be used as a secondary assay to test a candidate IGF modulating agents that is initially identified using another assay system such as a cell-free assay system. A cell proliferation assay may also be used to test whether CDK9 function plays a direct role in cell proliferation or cell cycle. For example, a cell proliferation or cell cycle assay may be performed on cells that over- or under-express CDK9 relative to wild type cells. Differences in proliferation or cell cycle compared to wild type cells suggests that the CDK9 plays a direct role in cell proliferation or cell cycle.

Angiogenesis.

Angiogenesis may be assayed using various human endothelial cell systems, such as umbilical vein, coronary artery, or dermal cells. Suitable assays include Alamar Blue based assays (available from Biosource International) to measure proliferation; migration assays using fluorescent molecules, such as the use of Becton Dickinson Falcon HTS FluoroBlock cell culture inserts to measure migration of cells through membranes in presence or absence of angiogenesis enhancer or suppressors; and tubule formation assays based on the formation of tubular structures by endothelial cells on Matrigel® (Becton Dickinson). Accordingly, an angiogenesis assay system may comprise a cell that expresses a CDK9, and that optionally has defective IGF function (e.g. IGF is over-expressed or under-expressed relative to wild-type cells). A test agent can be added to the angiogenesis assay system and changes in angiogenesis relative to controls where no test agent is added, identify candidate IGF modulating agents. In some embodiments of the invention, the angiogenesis assay may be used as a secondary assay to test a candidate IGF modulating agents that is initially identified using another assay system. An angiogenesis assay may also be used to test whether CDK9 function plays a direct role in cell proliferation. For example, an angiogenesis assay may be performed on cells that over- or under-express CDK9 relative to wild type cells. Differences in angiogenesis compared to wild type cells suggests that the CDK9 plays a direct role in angiogenesis. U.S. Pat. Nos. 5,976,782, 6,225,118 and 6,444,434, among others, describe various angiogenesis assays.

Hypoxic Induction.

The alpha subunit of the transcription factor, hypoxia inducible factor-1 (HIF-1), is upregulated in tumor cells following exposure to hypoxia in vitro. Under hypoxic conditions, HIF-1 stimulates the expression of genes known to be important in tumour cell survival, such as those-encoding glyolytic enzymes and VEGF. Induction of such genes by hypoxic conditions may be assayed by growing cells transfected with CDK9 in hypoxic conditions (such as with 0.1% O2, 5% CO2, and balance N2, generated in a Napco 7001 incubator (Precision Scientific)) and normoxic conditions, followed by assessment of gene activity or expression by Taqman®. For example, a hypoxic induction assay system may comprise a cell that expresses a CDK9, and that optionally has defective IGF function (e.g. IGF is over-expressed or under-expressed relative to wild-type cells). A test agent can be added to the hypoxic induction assay system and changes in hypoxic response relative to controls where no test agent is added, identify candidate IGF modulating agents. In some embodiments of the invention, the hypoxic induction assay may be used as a secondary assay to test a candidate IGF modulating agents that is initially identified using another assay system. A hypoxic induction assay may also be used to test whether CDK9 function plays a direct role in the hypoxic response. For example, a hypoxic induction assay may be performed on cells that over- or under-express CDK9 relative to wild type cells. Differences in hypoxic response compared to wild type cells suggests that the CDK9 plays a direct role in hypoxic induction.

Cell Adhesion.

Cell adhesion assays measure adhesion of cells to purified adhesion proteins, or adhesion of cells to each other, in presence or absence of candidate modulating agents. Cell-protein adhesion assays measure the ability of agents to modulate the adhesion of cells to purified proteins. For example, recombinant proteins are produced, diluted to 2.5 g/mL in PBS, and used to coat the wells of a microtiter plate. The wells used for negative control are not coated. Coated wells are then washed, blocked with 1% BSA, and washed again. Compounds are diluted to 2× final test concentration and added to the blocked, coated wells. Cells are then added to the wells, and the unbound cells are washed off. Retained cells are labeled directly on the plate by adding a membrane-permeable fluorescent dye, such as calcein-AM, and the signal is quantified in a fluorescent microplate reader.

Cell-cell adhesion assays measure the ability of agents to modulate binding of cell adhesion proteins with their native ligands. These assays use cells that naturally or recombinantly express the adhesion protein of choice. In an exemplary assay, cells expressing the cell adhesion protein are plated in wells of a multiwell plate. Cells expressing the ligand are labeled with a membrane-permeable fluorescent dye, such as BCECF, and allowed to adhere to the monolayers in the presence of candidate agents. Unbound cells are washed off, and bound cells are detected using a fluorescence plate reader.

High-throughput cell adhesion assays have also been described. In one such assay, small molecule ligands and peptides are bound to the surface of microscope slides using a microarray spotter, intact cells are then contacted with the slides, and unbound cells are washed off. In this assay, not only the binding specificity of the peptides and modulators against cell lines are determined, but also the functional cell signaling of attached cells using immunofluorescence techniques in situ on the microchip is measured (Falsey J R et al., Bioconjug Chem. 2001 May-June; 12(3):346-53).

Primary Assays for Antibody Modulators

For antibody modulators, appropriate primary assays test is a binding assay that tests the antibody's affinity to and specificity for the CDK9 protein. Methods for testing antibody affinity and specificity are well known in the art (Harlow and Lane, 1988, 1999, supra). The enzyme-linked immunosorbant assay (ELISA) is a preferred method for detecting CDK9-specific antibodies; others include FACS assays, radioimmunoassays, and fluorescent assays.

In some cases, screening assays described for small molecule modulators may also be used to test antibody modulators.

Primary Assays for Nucleic Acid Modulators

For nucleic acid modulators, primary assays may test the ability of the nucleic acid modulator to inhibit or enhance CDK9 gene expression, preferably mRNA expression. In general, expression analysis comprises comparing CDK9 expression in like populations of cells (e.g., two pools of cells that endogenously or recombinantly express CDK9) in the presence and absence of the nucleic acid modulator. Methods for analyzing mRNA and protein expression are well known in the art. For instance, Northern blotting, slot blotting, ribonuclease protection, quantitative RT-PCR (e.g., using the TaqMan®, PE Applied Biosystems), or microarray analysis may be used to confirm that CDK9 mRNA expression is reduced in cells treated with the nucleic acid modulator (e.g., Current Protocols in Molecular Biology (1994) Ausubel F M et al., eds., John Wiley & Sons, Inc., chapter 4; Freeman W M et al., Biotechniques (1999) 26:112-125; Kallioniemi O P, Ann Med 2001, 33:142-147; Blohm D H and Guiseppi-Elie, A Curr Opin Biotechnol 2001, 12:41-47). Protein expression may also be monitored. Proteins are most commonly detected with specific antibodies or antisera directed against either the CDK9 protein or specific peptides. A variety of means including Western blotting, ELISA, or in situ detection, are available (Harlow E and Lane D, 1988 and 1999, supra).

In some cases, screening assays described for small molecule modulators, particularly in assay systems that involve CDK9 mRNA expression, may also be used to test nucleic acid modulators.

Secondary Assays

Secondary assays may be used to further assess the activity of CDK9-modulating agent identified by any of the above methods to confirm that the modulating agent affects CDK9 in a manner relevant to the IGF pathway. As used herein, CDK9-modulating agents encompass candidate clinical compounds or other agents derived from previously identified modulating agent. Secondary assays can also be used to test the activity of a modulating agent on a particular genetic or biochemical pathway or to test the specificity of the modulating agent's interaction with CDK9.

Secondary assays generally compare like populations of cells or animals (e.g., two pools of cells or animals that endogenously or recombinantly express CDK9) in the presence and absence of the candidate modulator. In general, such assays test whether treatment of cells or animals with a candidate CDK9-modulating agent results in changes in the IGF pathway in comparison to untreated (or mock- or placebo-treated) cells or animals. Certain assays use "sensitized genetic backgrounds", which, as used herein, describe cells or animals engineered for altered expression of genes in the IGF or interacting pathways.

Cell-Based Assays

Cell based assays may detect endogenous IGF pathway activity or may rely on recombinant expression of IGF pathway components. Any of the aforementioned assays may be used in this cell-based format. Candidate modulators are typically added to the cell media but may also be injected into cells or delivered by any other efficacious means.

Animal Assays

A variety of non-human animal models of normal or defective IGF pathway may be used to test candidate CDK9 modulators. Models for defective IGF pathway typically use genetically modified animals that have been engineered to mis-express (e.g., over-express or lack expression in) genes involved in the IGF pathway. Assays generally require systemic delivery of the candidate modulators, such as by oral administration, injection, etc.

In a preferred embodiment, IGF pathway activity is assessed by monitoring neovascularization and angiogenesis. Animal models with defective and normal IGF are used to test the candidate modulator's affect on CDK9 in Matrigel® assays. Matrigel® is an extract of basement membrane proteins, and is composed primarily of laminin, collagen IV, and heparin sulfate proteoglycan. It is provided as a sterile liquid at 4° C., but rapidly forms a solid gel at 37° C. Liquid Matrigel® is mixed with various angiogenic agents, such as bFGF and VEGF, or with human tumor cells which over-express the CDK9. The mixture is then injected subcutaneously (SC) into female athymic nude mice (Taconic, Germantown, N.Y.) to support an intense vascular response. Mice with Matrigel® pellets may be dosed via oral (PO), intraperitoneal (IP), or intravenous (IV) routes with the candidate modulator. Mice are euthanized 5-12 days post-injection, and the Matrigel® pellet is harvested for hemoglobin analysis (Sigma plasma hemoglobin kit). Hemoglobin content of the gel is found to correlate the degree of neovascularization in the gel.

In another preferred embodiment, the effect of the candidate modulator on CDK9 is assessed via tumorigenicity assays. Tumor xenograft assays are known in the art (see, e.g., Ogawa K et al., 2000, Oncogene 19:6043-6052). Xenografts are typically implanted SC into female athymic mice, 6-7 week old, as single cell suspensions either from a pre-existing tumor or from in vitro culture. The tumors which express the CDK9 endogenously are injected in the flank, $1 \times 10^5$ to $1 \times 10^7$ cells per mouse in a volume of 100 μL using a 27 gauge needle. Mice are then ear tagged and tumors are measured twice weekly. Candidate modulator treatment is initiated on the day the mean tumor weight reaches' 100 mg. Candidate modulator is delivered IV, SC, IP, or PO by bolus administration. Depending upon the pharnacokinetics of each unique candidate modulator, dosing can be performed multiple times per day. The tumor weight is assessed by measuring perpendicular diameters with a caliper and calculated by multiplying the measurements of diameters in two dimensions. At the end of the experiment, the excised tumors maybe utilized for biomarker identification or further analyses. For immunohistochemistry staining, xenograft tumors are fixed in 4% paraformaldehyde, 0.1M phosphate, pH 7.2, for 6 hours at 4° C., immersed in 30% sucrose in PBS, and rapidly frozen in isopentane cooled with liquid nitrogen.

In another preferred embodiment, tumorogenicity is monitored using a hollow fiber assay, which is described in U.S. Pat. No. 5,698,413. Briefly, the method comprises implanting into a laboratory animal a biocompatible, semi-permeable encapsulation device containing target cells, treating the laboratory animal with a candidate modulating agent, and evaluating the target cells for reaction to the candidate modulator. Implanted cells are generally human cells from a preexisting tumor or a tumor cell line. After an appropriate period of time, generally around six days, the implanted samples are harvested for evaluation of the candidate modulator. Tumorogenicity and modulator efficacy may be evaluated by assaying the quantity of viable cells present in the macrocapsule, which can be determined by tests known in the art, for example, MTT dye conversion assay, neutral red dye uptake, trypan blue staining, viable cell counts, the number of colonies formed in soft agar, the capacity of the cells to recover and replicate in vitro, etc.

In another preferred embodiment, a tumorogenicity assay use a transgenic animal, usually a mouse, carrying a dominant oncogene or tumor suppressor gene knockout under the control of tissue specific regulatory sequences; these assays are generally referred to as transgenic tumor assays. In a preferred application, tumor development in the transgenic model is well characterized or is controlled. In an exemplary model, the "RIP1-Tag2" transgene, comprising the SV40 large T-antigen oncogene under control of the insulin gene regulatory regions is expressed in pancreatic beta cells and results in islet cell carcinomas (Hanahan D, 1985, Nature 315:115-122; Parangi S et al, 1996, Proc Natl Acad Sci USA 93: 2002-2007; Bergers G et al, 1999, Science 284:808-812). An "angiogenic switch," occurs at approximately five weeks, as normally quiescent capillaries in a subset of hyperproliferative islets become angiogenic. The RIP1-TAG2 mice die by age 14 weeks. Candidate modulators may be administered at a variety of stages, including just prior to the angiogenic switch (e.g., for a model of tumor prevention), during the growth of small tumors (e.g., for a model of intervention), or during the growth of large and/or invasive tumors (e.g., for a model of regression). Tumorogenicity and modulator efficacy can be evaluating life-span extension and/or tumor characteristics, including number of tumors, tumor size, tumor morphology, vessel density, apoptotic index, etc.

Diagnostic and Therapeutic Uses

Specific CDK9-modulating agents are useful in a variety of diagnostic and therapeutic applications where disease or disease prognosis is related to defects in the IGF pathway, such as angiogenic, apoptotic, or cell proliferation disorders. Accordingly, the invention also provides methods for modulating the IGF pathway in a cell, preferably a cell pre-determined to have defective or impaired IGF function (e.g. due to overexpression, underexpression, or misexpression of IGF, or due to gene mutations), comprising the step of administering an agent to the cell that specifically modulates CDK9 activity. Preferably, the modulating agent produces a detectable phenotypic change in the cell indicating that the IGF function is restored. The phrase "function is restored", and equivalents, as used herein, means that the desired phenotype is achieved, or is brought closer to normal compared to untreated cells. For example, with restored IGF function, cell proliferation and/or progression through cell cycle may normalize, or be brought closer to normal relative to untreated cells. The invention also provides methods for treating disorders or disease associated with impaired IGF function by administering a therapeutically effective amount of a CDK9-modulating agent that modulates the IGF pathway. The invention further provides methods for modulating CDK9 function in a cell, preferably a cell pre-determined to have defective or impaired CDK9 function, by administering a CDK9-modulating agent. Additionally, the invention provides a method for treating disorders or disease associated with impaired CDK9 function by administering a therapeutically effective amount of a CDK9-modulating agent.

The discovery that CDK9 is implicated in IGF pathway provides for a variety of methods that can be employed for the diagnostic and prognostic evaluation of diseases and disorders involving defects in the IGF pathway and for the identification of subjects having a predisposition to such diseases and disorders.

Various expression analysis methods can be used to diagnose whether CDK9 expression occurs in a particular sample, including Northern blotting, slot blotting, ribonuclease protection, quantitative RT-PCR, and microarray analysis. (e.g., Current Protocols in Molecular Biology (1994) Ausubel F M et al., eds., John Wiley & Sons, Inc., chapter 4; Freeman W M et al., Biotechniques (1999) 26:112-125; Kallioniemi O P, Ann Med 2001, 33:142-147; Blohm and Guiseppi-Elie, Curr Opin Biotechnol 2001, 12:41-47). Tissues having a disease or disorder implicating defective IGF signaling that express a CDK9, are identified as amenable to treatment with a CDK9 modulating agent. In a preferred application, the IGF defective tissue overexpresses a CDK9 relative to normal tissue. For example, a Northern blot analysis of mRNA from tumor and normal cell lines, or from tumor and matching normal tissue samples from the same patient, using full or partial CDK9 cDNA sequences as probes, can determine whether particular tumors express or overexpress CDK9. Alternatively, the TaqMan® is used for quantitative RT-PCR analysis of CDK9 expression in cell lines, normal tissues and tumor samples (PE Applied Biosystems).

Various other diagnostic methods may be performed, for example, utilizing reagents such as the CDK9 oligonucleotides, and antibodies directed against a CDK9, as described above for: (1) the detection of the presence of CDK9 gene mutations, or the detection of either over- or under-expression of CDK9 mRNA relative to the non-disorder state; (2) the detection of either an over- or an under-abundance of CDK9 gene product relative to the non-disorder state; and (3) the detection of perturbations or abnormalities in the signal transduction pathway mediated by CDK9.

Kits for detecting expression of CDK9 in various samples, comprising at least one antibody specific to CDK9, all reagents and/or devices suitable for the detection of antibodies, the immobilization of antibodies, and the like, and instructions for using such kits in diagnosis or therapy are also provided.

Thus, in a specific embodiment, the invention is drawn to a method for diagnosing a disease or disorder in a patient that is associated with alterations in CDK9 expression, the method comprising: a) obtaining a biological sample from the patient; b) contacting the sample with a probe for CDK9 expression; c) comparing results from step (b) with a control; and d) determining whether step (c) indicates a likelihood of the disease or disorder. Preferably, the disease is cancer, most preferably pancreatic cancer. The probe may be either DNA or protein, including an antibody.

EXAMPLES

The following experimental section and examples are offered by way of illustration and not by way of limitation.

I. *Drosophila* Cell IGF Screen

RNA interference (RNAi) was used to create dPTEN-deficient cultured *Drosophila* cells (Schneider S2 cells (Schneider, I. (1972) J. Embryol. Exp. Morph. 27, 363), adapted to serum-free media, from Invitrogen Corp., Carlsbad, Calif.). Cells were treated for 3 days with dPTEN double stranded RNA (dsRNA) or a control dsRNA representing sequences from a *Renilla luciferase* cDNA. After a 3 day dsRNA pretreatment, 1 µM bovine insulin was added to cells treated with dPTEN dsRNA to provide additional stimulation of the IGF/insulin pathway. PTEN-deficient, insulin-stimulated cells and control cells were plated in 384-well format and dsRNA representing approximately 10,000 different *Drosophila* genes were added to individual wells. A cell proliferation assay (AqueousOne™ assay—Promega Corp, Madison, Wis.) was used to quantify cell viability after 96-hours incubation. For each of the greater than 6000 dsRNA sequences tested in this manner, cell viability data was obtained on dPTEN-deficient, insulin-stimulated cells (insulin and dPTEN dsRNA-treated) and control cells (*Renilla luciferase* dsRNA-treated). Comparison of this data for each dsRNA identified dsRNA sequences that preferentially reduced the viability of insulin and dPTEN dsRNA treated cells. Additionally, the screen identified sequences that when inactivated, preferentially suppressed insulin induced LDH (lactate dehydrogenase) expression relative to normal cells. The LDH expression leves were detected by TaqMan® analysis.

Dmel cells were treated with 1 µM bovine insulin to stimulate the IGF/insulin pathway. The insulin-stimulated cells were plated into 384-well plates and dsRNA representing approximately 10,000 different *Drosophila* genes were added to individual wells. After a 96-hour incubation cells were lysed using Cells-to-cDNAII cell lysis buffer (Ambion) and a 384 format, multiplexed, RT-PCR TaqMan® assay was run on the lysates. The TaqMan® assay identifies changes in expression of lactate dehydrogenase, a IGF reporter gene, and Rp49, an internal standard to normalize values for cell number and RT-PCR efficiency. For each of the greater than 13,000 dsRNA sequences tested in this manner, effects on LDH and rp49 expression were analyzed. Selections of genes with the greatest reduction in LDH expression were further analyzed in a multiplexed Western Blot assay that examines phosphorylation and overall levels of several proteins simultaneously. The multiplexed assay measured changes in phosphorylation of 4E-BP1 (Thr37/46), MAPK1 (Thr202/Tyr204) and either S6K (Thr389) phosphorylation or total RPS6 protein levels. The multiplexed Western assay was done on lysates from cells treated with 1 µM insulin plated in 96 format and treated with target dsRNA for 96 hrs. Each lysate was tested for its differences in phosphorylation of 4E-BP 1 (Thr37/46), MAPK1 (Thr202/Tyr204), and either S6K (Thr389) phosphorylation or total RPS6 protein relative to negative control dsRNA (luciferase dsRNA). The quantitative Western blot assay, like the LDH reporter assay, was validated as a readout for IGF signaling by RNAi of known pathway components. CG5179-PA was a suppressor of LDH reporter gene expression. Orthologs of the modifier are referred to herein as CDK9.

BLAST analysis (Altschul et al., supra) was employed to identify orthologs of *Drosophila* modifiers. For example, representative sequence from CDK9, GI#4502747 (SEQ ID NO:6), shares 71% amino acid identity with the *Drosophila* CG5179-PA.

Various domains, signals, and functional subunits in proteins were analyzed using the PSORT (Nakai K., and Horton P., Trends Biochem Sci, 1999, 24:34-6; Kenta Nakai, Protein sorting signals and prediction of subcellular localization, Adv. Protein Chem. 54, 277-344 (2000)), PFAM (Bateman A., et al., Nucleic Acids Res, 1999, 27:260-2), SMART (Ponting C P, et al., SMART: identification and annotation of domains from signaling and extracellular protein sequences. Nucleic Acids Res. 1999 Jan. 1; 27(1):229-32), TM-HMM (Erik L. L. Sonnhammer, Gunnar von Heijne, and Anders Krogh: A hidden Markov model for predicting transmembrane helices in protein sequences. In Proc. of Sixth Int. Conf. on Intelligent Systems for Molecular Biology, p 175-182 Ed J. Glasgow, T. Littlejohn, F. Major, R. Lathrop, D. Sankoff, and C. Sensen Menlo Park, Calif.: AAAI Press, 1998), and clust (Remm M, and Sonnhammer E. Classification of transmembrane protein families in the Caenorhabditis elegans genome and identification of human orthologs. Genome Res. 2000 November; 10(11): 1679-89) programs. For example, the kinase domain (PFAM00069) of CDK9 from GI#4502747 (SEQ ID NO:6) is located at approximately amino acid residues 19 to 315.

II. High-Throughput In Vitro Fluorescence Polarization Assay

Fluorescently-labeled CDK9 peptide/substrate are added to each well of a 96-well microtiter plate, along with a test agent in a test buffer (10 mM HEPES, 10 mM NaCl, 6 mM magnesium chloride, pH 7.6). Changes in fluorescence polarization, determined by using a Fluorolite FPM-2 Fluorescence Polarization Microtiter System (Dynatech Laboratories, Inc), relative to control values indicates the test compound is a candidate modifier of CDK9 activity.

III. High-Throughput In Vitro Binding Assay.

$^{33}$P-labeled CDK9 peptide is added in an assay buffer (100 mM KCl, 20 mM HEPES pH 7.6, 1 mM MgCl$_2$, 1% glycerol, 0.5% NP-40, 50 mM beta-mercaptoethanol, 1 mg/ml BSA, cocktail of protease inhibitors) along with a test agent to the wells of a Neutralite-avidin coated assay plate and incubated at 25° C. for 1 hour. Biotinylated substrate is then added to each well and incubated for 1 hour. Reactions are stopped by washing with PBS, and counted in a scintillation counter. Test agents that cause a difference in activity relative to control without test agent are identified as candidate IGF modulating agents.

IV. Immunoprecipitations and Immunoblotting

For coprecipitation of transfected proteins, $3 \times 10^6$ appropriate recombinant cells containing the CDK9 proteins are plated on 10-cm dishes and transfected on the following day with expression constructs. The total amount of DNA is kept constant in each transfection by adding empty vector. After 24 h, cells are collected, washed once with phosphate-buffered saline and lysed for 20 min on ice in 1 ml of lysis buffer containing 50 mM Hepes, pH 7.9, 250 mM NaCl, 20 mM-glycerophosphate, 1 mM sodium orthovanadate, 5 mM p-nitrophenyl phosphate, 2 mM dithiothreitol, protease inhibitors (complete, Roche Molecular Biochemicals), and 1% Nonidet P-40. Cellular debris is removed by centrifugation twice at 15,000×g for 15 min. The cell lysate is incubated with 25 µl of M2 beads (Sigma) for 2 h at 4° C. with gentle rocking.

After extensive washing with lysis buffer, proteins bound to the beads are solubilized by boiling in SDS sample buffer, fractionated by SDS-polyacrylamide gel electrophoresis, transferred to polyvinylidene difluoride membrane and blotted with the indicated antibodies. The reactive bands are visualized with horseradish peroxidase coupled to the appropriate secondary antibodies and the enhanced chemiluminescence (ECL) Western blotting detection system (Amersham Pharmacia Biotech).

V. Kinase Assay

A purified or partially purified CDK9 is diluted in a suitable reaction buffer, e.g., 50 mM Hepes, pH 7.5, containing magnesium chloride or manganese chloride (1-20 mM) and a peptide or polypeptide substrate, such as myelin basic protein or casein (1-10 µg/ml). The final concentration of the kinase is 1-20 nM. The enzyme reaction is conducted in microtiter plates to facilitate optimization of reaction conditions by increasing assay throughput. A 96-well microtiter plate is employed using a final volume 30-100 µl. The reaction is initiated by the addition of $^{33}$P-gamma-ATP (0.5 µCi/ml) and incubated for 0.5 to 3 hours at room temperature. Negative controls are provided by the addition of EDTA, which chelates the divalent cation ($Mg^{2+}$ or $Mn^{2+}$) required for enzymatic activity. Following the incubation, the enzyme reaction is quenched using EDTA. Samples of the reaction are transferred to a 96-well glass fiber filter plate (MultiScreen, Millipore). The filters are subsequently washed with phosphate-buffered saline, dilute phosphoric acid (0.5%) or other suitable medium to remove excess radiolabeled ATP. Scintillation cocktail is added to the filter plate and the incorporated radioactivity is quantitated by scintillation counting (Wallac/Perkin Elmer). Activity is defined by the amount of radioactivity detected following subtraction of the negative control reaction value (EDTA quench).

VI. Expression Analysis

All cell lines used in the following experiments are NCI (National Cancer Institute) lines, and are available from ATCC (American Type Culture Collection, Manassas, Va. 20110-2209). Normal and tumor tissues were obtained from Impath, UC Davis, Clontech, Stratagene, Ardais, Genome Collaborative, and Ambion.

TaqMan® analysis was used to assess expression levels of the disclosed genes in various samples.

RNA was extracted from each tissue sample using Qiagen (Valencia, Calif.) RNeasy kits, following manufacturer's protocols, to a final concentration of 50 ng/µl. Single stranded cDNA was then synthesized by reverse transcribing the RNA samples using random hexamers and 500 ng of total RNA per reaction, following protocol 4304965 of Applied Biosystems (Foster City, Calif.).

Primers for expression analysis using TaqMan® assay (Applied Biosystems, Foster City, Calif.) were prepared according to the TaqMan® protocols, and the following criteria: a) primer pairs were designed to span introns to eliminate genomic contamination, and b) each primer pair produced only one product. Expression analysis was performed using a 7900HT instrument.

TaqMan® reactions were carried out following manufacturer's protocols, in 25 µl total volume for 96-well plates and 10 µl total volume for 384-well plates, using 300 nM primer and 250 nM probe, and approximately, 25 ng of cDNA. The standard curve for result analysis was prepared using a universal pool of human cDNA samples, which is a mixture of cDNAs from a wide variety of tissues so that the chance that a target will be present in appreciable amounts is good. The raw data were normalized using 18S rRNA (universally expressed in all tissues and cells).

For each expression analysis, tumor tissue samples were compared with matched normal tissues from the same patient. A gene was considered overexpressed in a tumor when the level of expression of the gene was 2 fold or higher in the tumor compared with its matched normal sample. In cases where normal tissue was not available, a universal pool of cDNA samples was used instead. In these cases, a gene was considered overexpressed in a tumor sample when the difference of expression levels between a tumor sample and the average of all normal samples from the same tissue type was greater than 2 times the standard deviation of all normal samples (i.e., Tumor−average (all normal samples)>2× STDEV (all normal samples)).

Results indicated that CDK9 was overexpressed in 58% of pancreatic cancer samples as compared with matched normal tissues. A modulator identified by an assay described herein can be further validated for therapeutic effect by administration to a tumor in which the gene is overexpressed. A decrease in tumor growth confirms therapeutic utility of the modulator. Prior to treating a patient with the modulator, the likelihood that the patient will respond to treatment can be diagnosed by obtaining a tumor sample from the patient, and assaying for expression of the gene targeted by the modulator. The expression data for the gene(s) can also be used as a diagnostic marker for disease progression. The assay can be performed by expression analysis as described above, by antibody directed to the gene target, or by any other available detection method.

VII. CDK9 Functional Assays

RNAi experiments were carried out to knock down expression of CDK9 (SEQ ID NO:1) in various cell lines using small interfering RNAs (siRNA, Elbashir et al, supra).

Effect of CDK9 RNAi on Cell Proliferation and Growth.

BrdU and Cell Titer-Glo™ assays, as described above, were employed to study the effects of decreased CDK9 expression on cell proliferation. The results of these experiments indicated that RNAi of CDK9 decreased proliferation in A549 lung cancer cells.

Standard colony growth assays, as described above, were employed to study the effects of decreased CDK9 expression on cell growth. The results of this experiment indicated that RNAi of CDK9 decreased proliferation in A2780 ovarian cancer and A549 lung cancer cells.

[$^3$H]-thymidine incorporation assay, as described above, was also employed to study the effects of decreased CDK9 expression on cell proliferation. The results of this experiment indicated that RNAi of CDK9 decreased proliferation in A2780 ovarian cancer cells.

Effect of CDK9 RNAi on Apoptosis.

The Phospho-histone H2B assay, as described above, was employed to study the effects of decreased CDK9 expression on apoptosis. The results of this experiment indicated that RNAi of CDK9 increased apoptosis in 231T breast cancer, A549 lung cancer, and PC3 prostate cancer cells. Further, cell count was also reduced in 231T and A549 cells.

Multiple paramater apoptosis assay, as described above, was also used to study the effects of decreased CDK9 expression on apoptosis. The results of this experiment indicated that RNAi of CDK9 increased apoptosis in A2780 ovarian cancer cells and A549 lung cancer cells.

Transcriptional Reporter Assays.

Transcriptional reporter assays were performed to measure the effects of overexpressed CDK9 on expression of various transcription factors. In this assay, rat intestinal epithelial cells (RIEs), rat kidney epithelail cells (RKE), or NIH3T3 cells were co-transfected with reporter constructs containing various transcription factors and luciferase along with CDK9. Luciferase intensity was then measured as the readout for transcriptional activation due to overexpression of the CDK9. Overexpressed CDK9 caused an increased expression of the following transcription factors: EGR (Early growth response) and E2F.

Involvement in PTEN/IGF Pathway:

CDK9 FOXO nuclear translocation assays. FOXO nuclear translocation assays, as described above, were employed to assess involvement of CDK9 in the PTEN/IGF pathway. In these experiments, cells with reduced expression of CDK9 by RNAi were transiently transfected with a plasmid expressing GFP-tagged FOXO. Automated imaging of cellular components, such as nucleus and cytoplasm were then carried out to assess translocation of FOXO. Alternatively, cells were co-transfected with siRNA directed to CDK9 along with a plasmid containing FOXO, and a cassette containing a promoter, a FOXO response element, and luciferase. Cells were then analyzed for luciferase activity and compared with cells with no siRNA. Results indicated that reduced expression of CDK9 led to translocation of FOXO to the cytoplasm, similar to loss of PTEN in A2780 ovarian cancer and PC3 prostate cancer cells. These results suggest involvement of CDK9 in the PTEN/IGF pathway.

Pan-AKT assays. This assay was developed to detect involvement of CDK9 in the PTEN/IGF pathway. The assay detects changes in phosphorylation for several substrates of AKT, such as PRAS40, BAD, 4EBP1, and RPS6. For this experiment, antibodies were raised against phosphorylated AKT substrates, including the consensus phosphorylated AKT substrate sequence RxRxxS/T. Expression levels of phosphorylated substrates were then quantitated at normal levels, in presence of a negative control, a positive control (AKT), and then with CDK9 knockout. For example, when AKT levels were reduced, expression of all its substrates was also reduced. Results indicated that reduced expression of CDK9 was similar to increased levels of AKT in 231T breast cancer and A549 lung cancer cells.

We used RPS6 assay for one subset of experiments. RPS6 is an IGF dependent substrate of AKT. IGF1 treatment increases cytoplasmic RPS6 levels. Alternatively, Lily compound LY294002, a PI3K inhibitor, reduces AKT and cytoplasmic RPS6 levels. Cells were plated in 96 well plates, transfected with RNAi for CDK9, fixed, treated with RPS6 antibody, and stained. Measurements were based on percentage of population of cells with increased or decreased staining compared with negative or positive control cells. Results of this experiment showed that reduced expression of CDK9 altered the level of phospho RPS6 protein in 231T breast cancer, A549 lung cancer, and PC3 prostate cancer cells, thus suggesting an involvement in the IGF pathway.

We used PRAS40 as the substrate for another subset of experiments. For this substrate, pathway inhibition causes decreased cytoplasmic staining and increased nuclear and perinuclear staining. Cells were plated in 96 well plates, transfected with RNAi for CDK9, fixed, treated with PRAS40 antibody, and stained. Measurements were based on percentage of population of cells with increased or decreased nuclear/cytoplasmic staining ratio compared with negative or positive control cells. Results of this experiment showed that reduced expression of CDK9-altered the level of phospho PRAS40 protein in 231T, A549, and PC3 cells, thus again suggesting an involvement in the IGF pathway.

We used BAD as the substrate for another subset of the experiments. For this substrate, AKT pathway inhibition causes decreased cytoplasmic staining and unchanged or increased nuclear staining. Cells were plated in 96 well plates, transfected with RNAi for CDK9, fixed, permeabilized and stained with anti-phospho-BAD antibody. Measurements were based on the percentage of the population of cells with a decreased Cytoplasmic/Nuclear staining ratio compared with negative or positive control cells. Results of this experiment showed that reduced expression of CDK9 caused a reduction in the level of phospho-BAD protein in the cytoplasm in 231T, A549, and PC3 cells, thus again suggesting an involvement in the IGF pathway. Taken together, the results of the pan-AKT assay suggest involvement of CDK9 in the PTEN/IGF pathway.

What is claimed is:

1. A method of identifying an insulin-like growth factor (IGF) pathway modulating agent, said method comprising the steps of:
  (a) providing a first assay system comprising cultured cells that express a polynucleotide encoding a cyclin-dependent kinase 9 (CDK9) polypeptide, wherein the cultured cells have defective IGF function;
  (b) contacting the cultured cells of step (a) with a test agent;
  (c) determining the expression of CDK9 in the cultured cells of step (b) and comparing it with the expression of CDK9 in control cells that have not been contacted with the test agent;
  (d) identifying the test agent as an IGF pathway modulating agent by detecting a difference in the expression of CDK9 in the presence or absence of the test agent;
  (e) providing a second assay system comprising cultured cells expressing CDK9, wherein the second assay system is capable of detecting a change in the IGF pathway and includes an assay selected from a Forkhead Box (FOXO) nuclear translocation assay, proline-rich Akt substrate of 40 kDa (PRAS40) assay, BCL2-associated agonist of cell death (BAD) assay, 4E Binding Protein 1 (4EBP1) assay, and Ribosomal Protein S6 (RPS6) assay;
  (f) contacting the cultured cells of step (e) with the test agent of step (b); and
  (g) detecting a change in the IGF pathway in the presence or absence of the test agent, wherein a change in the IGF pathway confirms the identification of the test agent as an IGF pathway modulating agent.

2. The method of claim 1 wherein the test agent is a nucleic acid modulator.

3. The method of claim 2 wherein the nucleic acid modulator is an antisense oligomer.

4. The method of claim 2, wherein the nucleic acid modulator is a phosphothioate morpholino oligomer (PMO).

5. The method of claim 1, wherein the defect in IGF function is a Phosphatase and Tensin Homolog (PTEN) deficiency.

6. The method of claim 2 wherein the nucleic acid modulator is a dsRNA or an siRNA.

* * * * *

SEQUENCE LISTING

<160> NUMBER OF SEQ ID NOS: 6

<210> SEQ ID NO 1
<211> LENGTH: 1791
<212> TYPE: DNA
<213> ORGANISM: Homo sapiens

<400> SEQUENCE: 1

```
cgcccgccgg aggggcctgg agtgcggcgg cggcgggacc cggagcagga gcggcggcag        60
cagcgactgg gggcggcggc ggcgcgttgg aggcggccat ggcaaagcag tacgactcgg       120
tggagtgccc tttttgtgat gaagtttcca aatacgagaa gctcgccaag atcggccaag       180
gcaccttcgg ggaggtgttc aaggccaggc accgcaagac cggccagaag gtggctctga       240
agaaggtgct gatggaaaac gagaaggagg ggttccccat tacagccttg cgggagatca       300
agatccttca gcttctaaaa cacgagaatg tggtcaactt gattgagatt tgtcgaacca       360
aagcttcccc ctataaccgc tgcaagggta gtatatacct ggtgttcgac ttctgcgagc       420
atgaccttgc tgggctgttg agcaatgttt tggtcaagtt cacgctgtct gagatcaaga       480
gggtgatgca gatgctgctt aacggcctct actacatcca cagaaacaag atcctgcata       540
gggacatgaa ggctgctaat gtgcttatca ctcgtgatgg ggtcctgaag ctggcagact       600
ttgggctggc ccgggccttc agcctggcca agaacagcca gcccaaccgc tacaccaacc       660
```

```
gtgtggtgac actctggtac cggcccccgg agctgttgct cggggagcgg gactacggcc    720
cccccattga cctgtggggt gctgggtgca tcatggcaga gatgtggacc cgcagcccca    780
tcatgcaggg caacacggag cagcaccaac tcgccctcat cagtcagctc tgcggctcca    840
tcacccctga ggtgtggcca aacgtggaca actatgagct gtacgaaaag ctggagctgg    900
tcaagggcca gaagcggaag gtgaaggaca ggctgaaggc ctatgtgcgt gacccatacg    960
cactggacct catcgacaag ctgctggtgc tggaccctgc ccagcgcatc gacagcgatg   1020
acgccctcaa ccacgacttc ttctggtccg accccatgcc ctccgacctc aagggcatgc   1080
tctccaccca cctgacgtcc atgttcgagt acttggcacc accgcgccgg aagggcagcc   1140
agatcaccca gcagtccacc aaccagagtc gcaatcccgc caccaccaac cagacggagt   1200
ttgagcgcgt cttctgaggg ccggcgcttg ccactagggc tcttgtgttt tttttcttct   1260
gctatgtgac ttgcatcgtg gagacagggc atttgagttt atatctctca tgcatatttt   1320
atttaatccc caccctgggc tctgggagca gcccgctgag tggactggag tggagcattg   1380
gctgagagac caggagggca ctggagctgt cttgtccttg ctggttttct ggatggttcc   1440
cagagggttt ccatgggta ggaggatggg ctcgcccacc agtgactttt tctaagagct   1500
cccggcgtgg tggaagaggg gacaggtccc tcacccaccc acaatcctat tctcgggctg   1560
agaaccctgc gtgaggacag ggctcgcctc aggaatgggc tgttttggc ctaaccctca   1620
gaaacactgg ggctggcaca aactcttggt ttcttcaaca ggagaatttt actgtgtttc   1680
ttttggttcc attgtttgga gacattcctg ggcacagttt ggtccgttag aattaaaagt   1740
tgaattttt tttttttta aaaaaaaaa aaaaaaaaa aaaaaaaaaa a               1791

<210> SEQ ID NO 2
<211> LENGTH: 1753
<212> TYPE: DNA
<213> ORGANISM: Homo sapiens

<400> SEQUENCE: 2
cccggagcag gagcggcggc agcagcgact gggggcggcg gcggcgcgtt ggaggcggcc     60
atggcgaagc agtacgactc ggtggagtgc ccttttgtg atgaagtttc caaatacgag    120
aagctcgcca agatcggcca aggcaccttc ggggaggtgt tcaaggccag gcaccgcaag    180
accggccaga aggtggctct gaagaaggtg ctgatggaaa cgagaaggaa ggggttcccc    240
attacagcct gcgggagat caagatcctt cagcttctaa acacgagaa tgtggtcaac    300
ttgattgaga tttgtcgaac caaagcttcc ccctataacc gctgcaaggg tagtatatac    360
ctggtgttcg acttctgcga gcatgacctt gctgggctgt tgagcaatgt tttggtcaag    420
ttcacgctgt ctgagatcaa gagggtgatg cagatgctgc ttaacggcct ctactacatc    480
cacagaaaca agatcctgca tagggacatg aaggctgcta atgtgcttat cactcgtgat    540
ggggtcctga agctggcaga cttttgggctg gccccggcct tcagcctggc caagaacagc    600
cagcccaacc gctacaccaa ccgtgtggtg acactctggt accggccccc ggagctgttg    660
ctcggggagc gggactacgg ccccccccatt gacctgtggg gtgctgggtg catcatggca    720
gagatgtgga cccgcagccc catcatgcag ggcaacacgg agcagcacca actcgccctc    780
atcagtcagc tctgcggctc catcacccct gaggtgtggc aaacgtggac aactatgag    840
ctgtacgaaa agctggagct ggtcaagggc cagaagcgga aggtgaagga caggctgaag    900
gcctatgtgc gtgacccata cgcactggac ctcatcgaca agctgctggt gctggaccct    960
gcccagcgca tcgacagcga tgacgccctc aaccacgact tcttctggtc cgaccccatg   1020
```

| | | |
|---|---|---|
| ccctccgacc tcaagggcat gctctccacc cacctgacgt ccatgttcga gtacttggca | 1080 | |
| ccaccgcgcc ggaagggcag ccagatcacc cagcagtcca ccaaccagag tcgcaatccc | 1140 | |
| gccaccacca accagacgga gtttgagcgc gtcttctgag ggccggcgct tgccactagg | 1200 | |
| gctcttgtgt ttttttctt ctgctatgtg acttgcatcg tggagacagg catttgagt | 1260 | |
| ttatatctct catgcatatt ttatttaatc cccaccctgg gctctgggag cagcccgctg | 1320 | |
| agtggactgg agtggagcat tggctgagag accaggaggg cactggagct gtcttgtcct | 1380 | |
| tgctggtttt ctggatggtt cccagagggt ttccatgggg taggaggatg ggctcgccca | 1440 | |
| ccagtgactt tttctaagag ctcccggcgt ggtggaagag gggacaggtc cctcacccac | 1500 | |
| ccacaatcct attctcgggc tgagaaccct gcgtggggac agggctcgcc tcaggaatgg | 1560 | |
| gctgttttg gcctaaccct cagaaacact ggggctggca caaactcttg gtttcttcaa | 1620 | |
| caggagaatt ttactgtgtt tcttttggtt ccattgtttg gagacattcc tgggcacagt | 1680 | |
| ttggtccgtt agaattaaaa gttgaatttt tttttttttt taaaaaaaaa aaaaaaaaa | 1740 | |
| aaaaaaaaaa aaa | 1753 | |

<210> SEQ ID NO 3
<211> LENGTH: 5572
<212> TYPE: DNA
<213> ORGANISM: Homo sapiens

<400> SEQUENCE: 3

| | | |
|---|---|---|
| gatccacccg cagagggctg gagaggaggg ggcagattga agcggggcag aggaggcaga | 60 | |
| aaagacggct ttgctggagg ctgtccttgg gcagagctgg aggggggaatc tgggggccgc | 120 | |
| tggagccagg aagatgcgag ggaagggatg ggcgcgatgg gggagggaga tgggggggt | 180 | |
| gaacggtgag ctcgcgcctg cataaggaca gcaggcctcc ccactgctat cctcctggcc | 240 | |
| caacagcgaa tagcgtgagt caagagaatc ccctcactca gacacccagg ttcgggtccc | 300 | |
| aactttgtcg ccgtgtgacc ttgggcaaat gacctcacct ctgagcctca acgtcttctt | 360 | |
| ctgcaaaatg ggttagtgat cctgactatg ggctgttga ttcaggattc ggcgggaacg | 420 | |
| cccagcactt cctgagtaca caagagtgct gagaaaatgg tagctgtttt ttgcgattac | 480 | |
| tgactcgggg cccgaccagc tctggcacga ctcagcggag gtgggagtcc tgcgggtccc | 540 | |
| atccctgcct cccgaagagc cagacccag cgatagaagg cccgggcgtt gcttgctcgt | 600 | |
| cgccgctagt gccgccgcgc cccctggcgg ccgtcggttg ccatgtcaac ggagggtggc | 660 | |
| ggggaccggg ggaggcggag gcgggggccg ttctctcctc ccaggccggg aggacgctcc | 720 | |
| ctccgcgcct cccgccttcg cctctgtggg ggcactccga gccggggagg aagggggcttt | 780 | |
| ccgctgcagc cgacatgtgg gggtaaactg aggcacgcgg cagggcgccc gcagccaggt | 840 | |
| gccgagcgcg ggccccacc tccgaaggcg gaggagggc cgcgggcggt gacgcgccga | 900 | |
| gggcggccgc cggacagcga gcgggcgggc ggtggcggcg gcgcaggtg cggccgcgga | 960 | |
| gggtgggagg gaggagggcg gggcgggcg gaggaggagg ggagggcgag gccgggcacc | 1020 | |
| tccccctta taacgcgccc cctcttgggc tctcggccg tctcctagtc ggctcttccc | 1080 | |
| gtctcgcccc ctcgcccggc cgcccgggc ccgggtccgg ccaggagct cccaggccgc | 1140 | |
| ggctcggggg ctgacccccc gccgccgcc ccgcgcagcc cggcggaggc ggcgccgtcg | 1200 | |
| gaggaggagg agcagggcac tgcggctggc cccggatcgg gcgccagagc ggcagcagct | 1260 | |
| tcggcagcag cggcggcccg ggcccatgca gcggacgcg ccaccccgag ccccagctcc | 1320 | |
| ggcgccccgg ctccccgcgc cccgatcgg ggccgccgct agtagtggcg gcggcggagg | 1380 | |

| | |
|---|---|
| cgggggcagc ggcggcggcg gcggaggcgc ctctgcagct ccggctcccc ctggcctctc | 1440 |
| gggaactaca agtcccaggg ggcctggcgg tgggcggcgg gcggaagagg cggggtcggc | 1500 |
| gccgcgaggc cggaagtggc cgtggaggcg gaagtggcgc ggccgcggag gggcctggag | 1560 |
| tgcggcggcg gcgggacccg gagcaggagc ggcggcagca gcgactgggg gcggcggcgg | 1620 |
| cgcgttggag gcggccatgg caaagcagta cgactcggtg gagtgcccct tttgtgatga | 1680 |
| agtttccaaa tacgagaagc tcgccaagat cggccaaggc accttcgggt aaggctgggc | 1740 |
| ccctcgggc cgggagccct gggcctgcac ccctagggcc gacgtcggga tgcccgggcc | 1800 |
| ccccccgagt tggtagagaa gtcgtctgtc cccgggcttg cctgctggtc tctaggccgc | 1860 |
| gccgcacccc gccccggcct gacggagccg gctggtgggg aggagcctga ggcccgtggt | 1920 |
| gggggcgggg aggggctgca gagaggcgcc cgtgagggga gcgggatctc tccaagggac | 1980 |
| gcccaagtga ggagaaggga ctgagggaag gaagcagagg ctccgaacga gacaggctgc | 2040 |
| cgggtggcgg ggtagccgcg tgccctgggt acctagccca gccccgcccg ggaatctctt | 2100 |
| tgctgctgcc cctcctcctg tagtggggga ggggcgggcc ctgcggaaat ggcctgatga | 2160 |
| gttctcgggt ctccctttcc gcctgcaggg aggtgttcaa ggccaggcac cgcaagaccg | 2220 |
| gccagaaggt ggctctgaag aaggtgctga tggaaaacga gaaggagggg gtgagtacgg | 2280 |
| atcgggcgtg cgggccggcc ggctaactgc ccgggacccc gggtcggttt tccaccctgc | 2340 |
| tgcttctggg agtctcaggt tgagatttaa ttttttgta gtagttcaga aatttccagg | 2400 |
| gaatgtggct tccaccctaa aactaaatgt tcattctta ggcagttatg ggtgaggcca | 2460 |
| ggaggggag ttgatgcatg catcgtgtgc actttatttc acgaagttag gaagccttta | 2520 |
| aacaccttt tttagtgtta aatttcgctt aatgtaaaag aaagattata tatgcatgct | 2580 |
| ttttgaaagg tgtctgatac tcaattattt aatgtattta aaaggagcgg tcccttctcc | 2640 |
| accccatctt agctctagta caacttccca taaaccttct tttgcgtaat gtgcattagc | 2700 |
| aaggacattt ttaaatcatc atgtttgttg ccaacgaaac agccatagag ctgaaatttg | 2760 |
| aagactgaaa ccgccgagcg tttagtggct aatagcaaag tattgctgtt tcagtttgtt | 2820 |
| gtctcaaacc atcatcttga agtgtgcatg ctactaatat ccattttata gacaaggctt | 2880 |
| ctgagacagc tggtttcaga gcccatgatc ttgctctgtc tcccaacttg gctgtcagta | 2940 |
| cagaccccag ggctgggctc tgtactgcgc tcactcttga ccactttccc ctctttctca | 3000 |
| cccagttccc cattacagcc ttgcgggaga tcaagatcct tcagcttcta aaacacgaga | 3060 |
| atgtggtcaa cttgattgag atttgtcgaa ccaaaggtaa gttatttggt cttacgagaa | 3120 |
| gatgacactt gtacggtaag gttttgtttg taaacttgga actaggcaca cctaaactgc | 3180 |
| ctcttcttaa ctcagatgga cccatggtga ctgcttttc tggtcctctt tcatcgtagc | 3240 |
| tggtgcttcc tcggggcctg ccctggccca aagaggcac tcagaaaata tttgaccggt | 3300 |
| gaaggaagga acagacagat gctctggagg gcatgggtgc ccgtggggttg agcaggaag | 3360 |
| aaagaagctg gttgtgggaa agtgtgttgg gtgtggtttt cttgacttt tcttctttct | 3420 |
| attcctgcct cagcttcccc ctataaccgc tgcaagggta gtataacct ggtgttcgac | 3480 |
| ttctgcgagc atgaccttgc tgggctgttg agcaatgttt tggtcaagtt cacgctgtct | 3540 |
| gagatcaaga gggtgatgca gatgctgctt aacggcctct actacatcca cagaaacaag | 3600 |
| gtgggggcca gagctgggag gaggacccag gcttgggctg gtcttggctc ccactcccgg | 3660 |
| gtggatgtca ctaaaggacc cactcttgcc cttcctgcag atcctgcata gggacatgaa | 3720 |
| ggctgctaat gtgcttatca ctcgtgatgg ggtcctgaag ctggcagact ttgggctggc | 3780 |

```
ccgggccttc agcctggcca agaacagcca gcccaaccgc tacaccaacc gtgtggtgac    3840
actctggtac cggcccccgg agctgttgct cggtgaggac tcccgagcgg gccaaggggg    3900
gtgagggcca ggcatctacc tggccccttc cccccaactg ccagggcttc ttgagctgcc    3960
ggccctgggg cattgagcct caggaggccc tcgggctcaa ggggccctcc tggtgcgctc    4020
ttcttcccag gggagcggga ctacggcccc ccattgacc tgtggggtgc tgggtgcatc    4080
atggcagaga tgtggacccg cagccccatc atgcaggcca acacggagca gcaccaactc    4140
gccctcatca gtcagctctg cggctccatc accctgagg tacggggccc cggtccccac    4200
ggggtgcaga gatcgaggtc ccccggcaga ggaggagtgg ggagtagaat ggaaggagcg    4260
ctcctctctg gaagggaggc tggtttggtg acagggcctg tcttggggtg gggagtgtgt    4320
gggagaaaaa aacacctgac acaggctgtg cgccagtctc ggttccatca gctgttctgt    4380
ggccttgggc agaacatctg agtcagcgct gggtttctct tctgtgaacc agaaatgtga    4440
cgtgtatcag ggttggagcc catattccag gtgatgtggg tggaaggacc tggcacgtgg    4500
tatgtgccaa tccatagcgg gccactgctt ctgggagggg tcgagtagca gtctgggagc    4560
ctccgagtgg agcaggtatt ttagtccttt taggccttta tgaagggata agccacgcac    4620
ctcctgaccg gactccatat tctctcaacg cccctccct cccaggtgtg gccaaacgtg    4680
gacaactatg agctgtacga aaagctggag ctggtcaagg gccagaagcg gaaggtgaag    4740
gacaggctga aggcctatgt gcgtgaccca tacgcactgg acctcatcga caagctgctg    4800
gtgctggacc ctgcccagcg catcgacagc gatgacgccc tcaaccacga cttcttctgg    4860
tccgacccca tgccctccga cctcaagggc atgctctcca cccacctgac gtccatgttc    4920
gagtacttgg caccaccgcg ccggaagggc agccagatca cccagcagtc caccaaccag    4980
agtcgcaatc ccgccaccac caaccagacg gagtttgagc gcgtcttctg agggccggcg    5040
cttgccacta gggctcttgt gttttttttc ttctgctatg tgacttgcat cgtgggagaca    5100 gggcatttga gtttatatct ctcatgcata ttttatttaa tccccaccct gggctctggg    5160
agcagcccgc tgagtggact ggagtggagc attggctgag agaccaggag ggcactggag    5220
ctgtcttgtc cttgctggtt ttctggatgg ttcccagagg gtttcatgg ggtaggagga    5280 tgggctcgcc caccagtgac ttttttctaag agctcccggc gtggtggaag aggggacagg    5340
tccctcaccc acccacaatc ctattctcgg gctgagaacc ctgcgtgagg acagggctcg    5400
cctcaggaat gggctgtttt tggcctaacc ctcagaaaca ctggggctgg cacaaactct    5460
tggtttcttc aacaggagaa ttttactgtg tttcttttgg ttccattgtt tggagacatt    5520
cctgggcaca gtttggtccg ttagaattaa aagttgaatt tttaaaaaaa aa            5572
```

<210> SEQ ID NO 4
<211> LENGTH: 1758
<212> TYPE: DNA
<213> ORGANISM: Homo sapiens

<400> SEQUENCE: 4

```
cgcccgccgg aggggcctgg agtgcggcgg cggcgggacc cggagcagga gcggcggcag      60
cagcgactgg gggcggcggc ggcgcgttgg aggcggccat ggcaaagcag tacgactcgg     120
tggagtgccc ttttttgtgat gaagtttcca aatacgagaa gctcgccaag atcgccaag     180 gcaccttcgg ggaggtgttc aaggccaggc accgcaagac cggccagaag gtggctctga     240
agaaggtgct gatggaaaac gagaaggagg ggttccccat tacagccttg cgggagatca     300
agatccttca gcttctaaaa cacgagaatg tggtcaactt gattgagatt tgtcgaacca     360
```

-continued

```
aagcttcccc ctataaccgc tgcaagggta gtatatacct ggtgttcgac ttctgcgagc    420
atgaccttgc tgggctgttg agcaatgttt tggtcaagtt cacgctgtct gagatcaaga    480
gggtgatgca gatgctgctt aacggcctct actacatcca cagaaacaag atcctgcata    540
gggacatgaa ggctgctaat gtgcttatca ctcgtgatgg ggtcctgaag ctggcagact    600
ttgggctggc ccgggccttc agcctggcca agaacagcca gcccaaccgc tacaccaacc    660
gtgtggtgac actctggtac cggcccccgg agctgttgct cggggagcgg gactacggcc    720
cccccattga cctgtggggt gctgggtgca tcatggcaga gatgtggacc cgcagcccca    780
tcatgcaggc caacacggag cagcaccaac tcgccctcat cagtcagctc tgcggctcca    840
tcacccctga ggtgtggcca acgtggaca actatgagct gtacgaaaag ctggagctgg    900
tcaagggcca gaagcggaag gtgaaggaca ggctgaaggc ctatgtgcgt gacccatacg    960
cactggacct catcgacaag ctgctggtgc tggaccctgc ccagcgcatc gacagcgatg   1020
acgccctcaa ccacgacttc ttctggtccg accccatgcc ctccgacctc aagggcatgc   1080
tctccaccca cctgacgtcc atgttcgagt acttggcacc accgcgccgg aagggcagcc   1140
agatcaccca gcagtccacc aaccagagtc gcaatcccgc caccaccaac cagacggagt   1200
ttgagcgcgt cttctgaggg ccggcgcttg ccactagggc tcttgtgttt ttttttcttct  1260
gctatgtgac ttgcatcgtg gagacagggc atttgagttt atatctctca tgcatatttt   1320
atttaatccc caccctgggc tctgggagca gcccgctgag tggactggag tggagcattg   1380
gctgagagac caggagggca ctggagctgt cttgtccttg ctggttttct ggatggttcc   1440
cagagggttt ccatgggggta ggaggatggg ctcgcccacc agtgactttt tctaagagct   1500
cccggcgtgg tggaagaggg gacaggtccc tcacccaccc acaatcctat tctcgggctg   1560
agaaccctgc gtgaggacag ggctcgcctc aggaatgggc tgttttggc ctaaccctca    1620
gaaacactgg ggctggcaca aactcttggt ttcttcaaca ggagaatttt actgtgtttc   1680
ttttggttcc attgtttgga gacattcctg ggcacagttt ggtccgttag aattaaaagt   1740
tgaattttta aaaaaaa                                                  1758
```

<210> SEQ ID NO 5
<211> LENGTH: 1119
<212> TYPE: DNA
<213> ORGANISM: Homo sapiens

<400> SEQUENCE: 5

```
atggcaaagc agtacgactc ggtggagtgc ccttttttgtg atgaagtttc caaatacgag    60
aagctcgcca agatcggcca aggcaccttc ggggaggtgt tcaaggccag gcaccgcaag   120
accggccaga aggtggctct gaagaaggtg ctgatggaaa cgagaaggga ggggttcccc   180
attacagcct tgcgggagat caagatcctt cagcttctaa acacgagaa tgtggtcaac    240
ttgattgaga tttgtcgaac caaagcttcc ccctataacc gctgcaaggg tagtatatac    300
ctggtgttcg acttctgcga gcatgacctt gctgggctgt tgagcaatgt tttggtcaag   360
ttcacgctgt ctgagatcaa gagggtgatg cagatgctgc ttaacggcct ctactacatc    420
cacagaaaca agatcctgca tagggacatg aaggctgcta atgtgcttat cactcgtgat    480
ggggtcccga gctggcaga cttttgggctg gcccgggcct tcagcctggc caagaacagc   540
cagcccaacc gctacaccaa ccgtgtggtg acactctggt accggccccc ggagctgttg   600
ctcggggagc gggactacgg cccccccatt gacctgtggg gtgctgggtg catcatggca   660
gagatgtgga cccgcagccc catcatgcag gccaacacgg agcagcacca actcgccctc   720
```

-continued

```
atcagtcagc tctgcggctc catcacccct gaggtgtggc caaacgtgga caactatgag    780
ctgtacgaaa agctggagct ggtcaagggc cagaagcgga aggtgaagga caggctgaag    840
gcctatgtgc gtgacccata cgcactggac ctcatcgaca agctgctggt gctggaccct    900
gcccagcgca tcgacagcga tgacgccctc aaccacgact tcttctggtc cgaccccatg    960
ccctccgacc tcaagggcat gctctccacc cacctgacgt ccatgttcga gtacttggca   1020
ccaccgcgcc ggaagggcag ccagatcacc cagcagtcca ccaaccagag tcgcaatccc   1080
gccaccacca accagacgga gtttgagcgc gtcttctag                          1119
```

<210> SEQ ID NO 6
<211> LENGTH: 372
<212> TYPE: PRT
<213> ORGANISM: Homo sapiens

<400> SEQUENCE: 6

```
Met Ala Lys Gln Tyr Asp Ser Val Glu Cys Pro Phe Cys Asp Glu Val
 1               5                  10                  15

Ser Lys Tyr Glu Lys Leu Ala Lys Ile Gly Gln Gly Thr Phe Gly Glu
            20                  25                  30

Val Phe Lys Ala Arg His Arg Lys Thr Gly Gln Lys Val Ala Leu Lys
        35                  40                  45

Lys Val Leu Met Glu Asn Glu Lys Glu Gly Phe Pro Ile Thr Ala Leu
    50                  55                  60

Arg Glu Ile Lys Ile Leu Gln Leu Leu Lys His Glu Asn Val Val Asn
65                  70                  75                  80

Leu Ile Glu Ile Cys Arg Thr Lys Ala Ser Pro Tyr Asn Arg Cys Lys
                85                  90                  95

Gly Ser Ile Tyr Leu Val Phe Asp Phe Cys Glu His Asp Leu Ala Gly
            100                 105                 110

Leu Leu Ser Asn Val Leu Val Lys Phe Thr Leu Ser Glu Ile Lys Arg
        115                 120                 125

Val Met Gln Met Leu Leu Asn Gly Leu Tyr Tyr Ile His Arg Asn Lys
    130                 135                 140

Ile Leu His Arg Asp Met Lys Ala Ala Asn Val Leu Ile Thr Arg Asp
145                 150                 155                 160

Gly Val Leu Lys Leu Ala Asp Phe Gly Leu Ala Arg Ala Phe Ser Leu
                165                 170                 175

Ala Lys Asn Ser Gln Pro Asn Arg Tyr Thr Asn Arg Val Val Thr Leu
            180                 185                 190

Trp Tyr Arg Pro Pro Glu Leu Leu Gly Glu Arg Asp Tyr Gly Pro
        195                 200                 205

Pro Ile Asp Leu Trp Gly Ala Gly Cys Ile Met Ala Glu Met Trp Thr
    210                 215                 220

Arg Ser Pro Ile Met Gln Gly Asn Thr Glu Gln His Gln Leu Ala Leu
225                 230                 235                 240

Ile Ser Gln Leu Cys Gly Ser Ile Thr Pro Glu Val Trp Pro Asn Val
                245                 250                 255

Asp Asn Tyr Glu Leu Tyr Glu Lys Leu Glu Leu Val Lys Gly Gln Lys
            260                 265                 270

Arg Lys Val Lys Asp Arg Leu Lys Ala Tyr Val Arg Asp Pro Tyr Ala
        275                 280                 285

Leu Asp Leu Ile Asp Lys Leu Leu Val Leu Asp Pro Ala Gln Arg Ile
    290                 295                 300

Asp Ser Asp Asp Ala Leu Asn His Asp Phe Phe Trp Ser Asp Pro Met
```

-continued

```
            305                 310                 315                 320
Pro Ser Asp Leu Lys Gly Met Leu Ser Thr His Leu Thr Ser Met Phe
                325                 330                 335

Glu Tyr Leu Ala Pro Pro Arg Arg Lys Gly Ser Gln Ile Thr Gln Gln
            340                 345                 350

Ser Thr Asn Gln Ser Arg Asn Pro Ala Thr Thr Asn Gln Thr Glu Phe
            355                 360                 365

Glu Arg Val Phe
        370
```